(12) United States Patent
Asirvatham et al.

(10) Patent No.: US 10,098,695 B2
(45) Date of Patent: Oct. 16, 2018

(54) PERICARDIAL MODIFICATION DEVICES AND METHODS

(71) Applicant: Mayo Foundation for Medical Education and Research, Rochester, MN (US)

(72) Inventors: Samuel J. Asirvatham, Rochester, MN (US); Barry A. Borlaug, Rochester, MN (US); Christopher V. DeSimone, Rochester, MN (US); Prakriti Gaba, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 15/356,200

(22) Filed: Nov. 18, 2016

(65) Prior Publication Data

US 2017/0258521 A1    Sep. 14, 2017

Related U.S. Application Data

(60) Provisional application No. 62/414,281, filed on Oct. 28, 2016, provisional application No. 62/306,443, filed on Mar. 10, 2016.

(51) Int. Cl.
*A61B 18/14* (2006.01)
*A61B 5/053* (2006.01)
(Continued)

(52) U.S. Cl.
CPC .......... *A61B 18/1492* (2013.01); *A61B 5/021* (2013.01); *A61B 5/024* (2013.01);
(Continued)

(58) Field of Classification Search
CPC ... A61B 18/1492; A61B 8/0891; A61B 8/488; A61B 5/0538; A61B 5/0245;
(Continued)

(56) References Cited

U.S. PATENT DOCUMENTS 5,931,810 A    8/1999  Grabek
6,231,518 B1   5/2001  Grabek et al.
(Continued)

FOREIGN PATENT DOCUMENTS

JP    A-2007-509702    4/2007
WO    WO 2005/044079   5/2005
(Continued)

OTHER PUBLICATIONS

Belenkie et al., "Ventricular interaction: from bench to bedside," *Ann Med.*, 33(4):236-241, May 2001.
(Continued)

*Primary Examiner* — Mark W Bockelman
(74) *Attorney, Agent, or Firm* — Fish & Richardson P.C.

(57) ABSTRACT

Devices and methods are described for the treatment of heart conditions such as heart failure with preserved ejection fraction, including diastolic heart failure, by performing a pericardial modification procedure. Intraoperative test procedures for assessing the efficacy of the pericardial modification procedure are also described.

24 Claims, 17 Drawing Sheets

(51) Int. Cl.

| | | |
|---|---|---|
| *A61B 5/0245* | (2006.01) | |
| *A61B 17/3209* | (2006.01) | |
| *A61B 5/024* | (2006.01) | |
| *A61B 5/021* | (2006.01) | |
| *A61B 17/00* | (2006.01) | |
| *A61B 17/3201* | (2006.01) | |
| *A61B 8/08* | (2006.01) | |
| *A61B 5/0215* | (2006.01) | |
| *A61B 17/32* | (2006.01) | |
| *A61B 17/34* | (2006.01) | |
| *A61B 18/00* | (2006.01) | |
| *A61B 17/22* | (2006.01) | |
| *A61B 17/29* | (2006.01) | |
| *A61B 90/00* | (2016.01) | |

(52) U.S. Cl.
CPC .......... *A61B 5/0215* (2013.01); *A61B 5/0245* (2013.01); *A61B 5/0538* (2013.01); *A61B 8/0891* (2013.01); *A61B 8/488* (2013.01); *A61B 17/00234* (2013.01); *A61B 17/3201* (2013.01); *A61B 17/3209* (2013.01); *A61B 17/320016* (2013.01); *A61B 17/3478* (2013.01); *A61B 2017/00243* (2013.01); *A61B 2017/00247* (2013.01); *A61B 2017/22038* (2013.01); *A61B 2017/2906* (2013.01); *A61B 2017/320044* (2013.01); *A61B 2018/00351* (2013.01); *A61B 2018/00577* (2013.01); *A61B 2018/00601* (2013.01); *A61B 2090/08021* (2016.02)

(58) Field of Classification Search
CPC ....... A61B 5/0215; A61B 5/024; A61B 5/021; A61B 17/3209; A61B 17/3201; A61B 17/00234; A61B 2018/00577; A61B 2017/00247
See application file for complete search history.

(56) References Cited

U.S. PATENT DOCUMENTS

| | | | |
|---|---|---|---|
| 6,478,028 | B1 | 11/2002 | Paolitto et al. |
| 6,585,635 | B1 | 7/2003 | Aldrich |
| 6,599,526 | B2 * | 7/2003 | Dimitrijevich ......... A61L 15/40 424/422 |
| 7,226,440 | B2 | 6/2007 | Gelfand et al. |
| 7,270,669 | B1 | 9/2007 | Sra |
| 7,398,781 | B1 | 7/2008 | Chin |
| 8,545,387 | B2 | 10/2013 | Harrison et al. |
| 8,652,025 | B2 | 2/2014 | Laufer et al. |
| 9,173,705 | B2 | 11/2015 | Whayne et al. |
| 9,220,490 | B2 | 12/2015 | Guenst |
| 2002/0107514 | A1 | 8/2002 | Hooven |
| 2004/0102804 | A1 | 5/2004 | Chin |
| 2004/0138527 | A1 | 7/2004 | Bonner |
| 2006/0173441 | A1 | 8/2006 | Gelfand et al. |
| 2006/0247672 | A1 | 11/2006 | Vidlund |
| 2007/0083082 | A1 | 4/2007 | Kiser |
| 2010/0063475 | A1 | 3/2010 | Jahns |
| 2011/0112569 | A1 | 5/2011 | Friedman |
| 2012/0296153 | A1 | 11/2012 | Laufer et al. |
| 2013/0046305 | A1 | 2/2013 | Davies et al. |
| 2014/0053111 | A1 | 2/2014 | Beckman |
| 2014/0330263 | A1 | 11/2014 | De Canniere |
| 2015/0265304 | A1 | 9/2015 | Feldman et al. |
| 2015/0313634 | A1 | 11/2015 | Gross et al. |
| 2016/0015410 | A1 | 1/2016 | Asirvatham et al. |
| 2016/0058504 | A1 | 3/2016 | Davies et al. |

FOREIGN PATENT DOCUMENTS

| | | | |
|---|---|---|---|
| WO | WO 2011130456 | | 10/2011 |
| WO | WO 2014/164641 | * | 9/2014 |

OTHER PUBLICATIONS

Bhargava et al., "Influence of the pericardium on left ventricular diastolic pressure-volume curves in dogs with sustained volume overload," *Am Heart J.*, 105(6):995-1001, Jun. 1983.
Crawford et al., "Effect of the undisturbed pericardium on left ventricular size and performance during acute volume loading," *Am Heart J.*, 105(2):267-272, Feb. 1983.
Hammond et al., "Heart size and maximal cardiac output are limited by the pericardium," *Am J Physiol.*, 263(6 Pt 2):H1675-H1681, Dec. 1992.
Spadaro et al., "Pericardial modulation of right and left ventricular diastolic interaction," *Circ Res.*, 48(2):233-238, Feb. 1981.
Stray-Gundersen et al., "The effect of pericardiectomy on maximal oxygen consumption and maximal cardiac output in untrained dogs," *Circ Res.*, 58(4):523-530, Apr. 1986.
International Search Report and Written Opinion for PCT/US2014/023081, dated Jul. 9, 2014, 13 pages.
International Preliminary Report on Patentability for PCT/US2014/02081, dated Sep. 24, 2015, 8 pages.
European Search Report for Application No. 14778493.8, dated Sep. 30, 2016, 8 pages.
International Search Report and Written Opinion for PCT/US2017/21512, dated May 31, 2017, 12 pages.
Japanese Office Actin in International Application No. JP2016-501148, dated Dec. 20, 2017, (10 pages including English Translation).

* cited by examiner

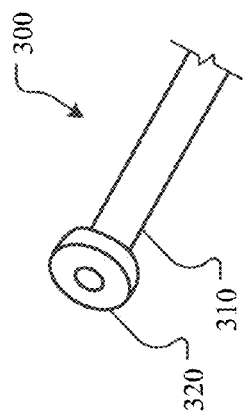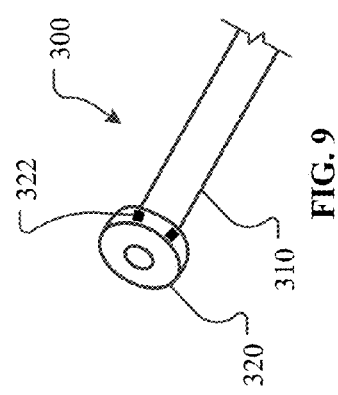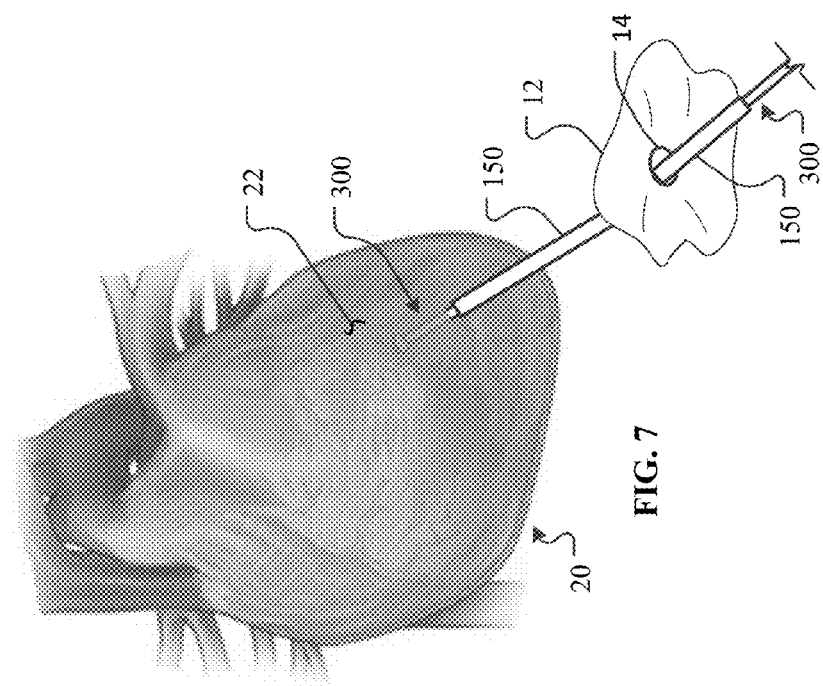

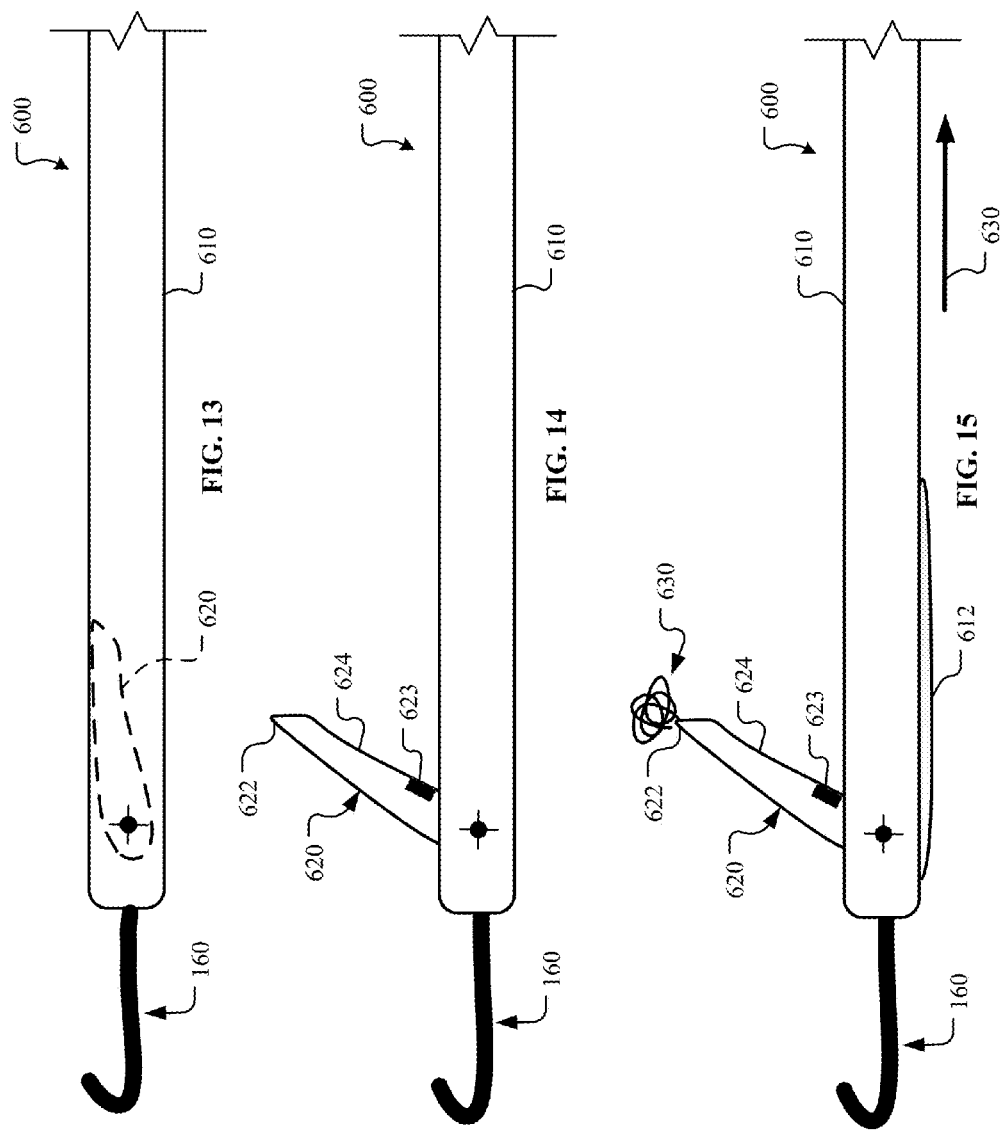

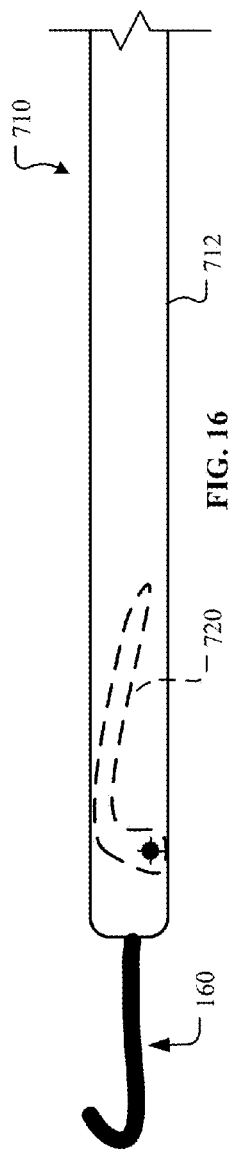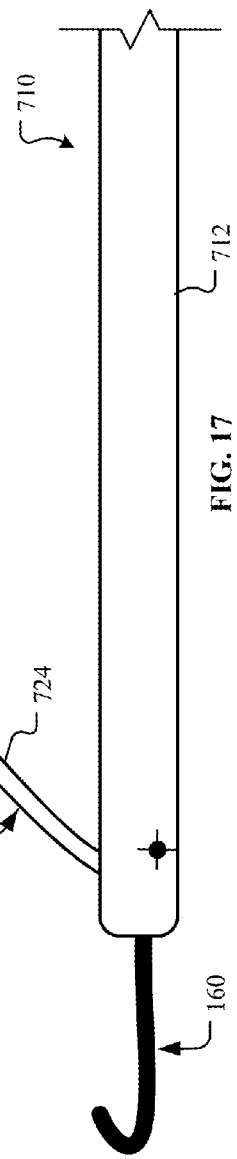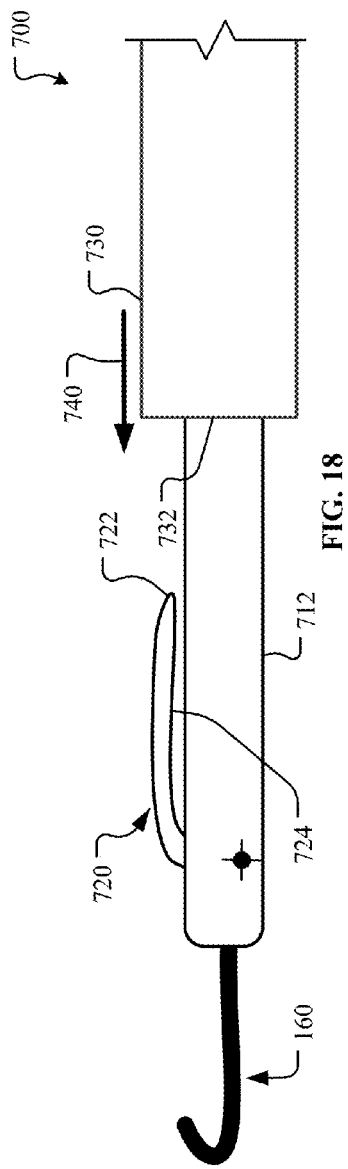

PERICARDIAL MODIFICATION DEVICES AND METHODS

CROSS-REFERENCE TO RELATED APPLICATIONS

This application claims the benefit of U.S. Provisional Application Ser. No. 62/414,281, filed Oct. 28, 2016, and U.S. Provisional Application Ser. No. 62/306,443, filed Mar. 10, 2016. The disclosures of the prior applications are considered part of (and are incorporated by reference in) the disclosure of this application.

BACKGROUND

1. Technical Field

This document relates to devices and methods for the treatment of heart conditions. For example, this document relates to devices and methods for treating heart failure with preserved ejection fraction, including diastolic heart failure, by performing a pericardial modification procedure.

2. Background Information

The pericardium is a thin double-layered fluid filled sac that surrounds the heart and the roots of the aorta, vena cava, and the pulmonary artery. The outer sac is known as the fibrous pericardium. The inner sac is known as the serous pericardium. The serous pericardium consists of a visceral layer portion and a parietal layer portion ("parietal pericardium"). The visceral layer covers the heart and the great vessels. The parietal portion lines the outer fibrous pericardium.

The phrenic nerves course from the brain to the diaphragm. The phrenic nerves provide motor impulses to muscles of the diaphragm, thereby allowing for lung expansion to facilitate breathing. The right phrenic nerve passes underneath the muscles of the neck and bones of the shoulder to the base of the right lung, contacting the heart and the trachea. The left phrenic nerve follows a similar path, passing close to the heart before entering the diaphragm.

SUMMARY

This document provides devices and methods for the treatment of heart conditions. For example, this document provides devices and methods for treating heart failure with preserved ejection fraction, including diastolic heart failure, by performing a pericardial modification procedure.

In one implementation, a dilator device includes a handle, a dilator shaft, and an energy conductor in electrical communication with the dilator shaft. The energy conductor is configured for attachment to an external energy source. A proximal end of the dilator shaft is coupled to the handle. The dilator shaft includes a distal tip portion that tapers to a point that is smaller than the diameter of the dilator shaft.

Such a dilator device may optionally include one or more of the following features. These features can be implemented alone or in combination for a given device. One or more electrodes may be disposed at the distal tip portion. At least a portion of the dilator shaft may be a dielectric member.

In another implementation, a method of puncturing pericardium includes the percutaneous insertion of a dilator device, placing the distal tip portion adjacent to the pericardium, energizing the energy conductor such that at least the point emits an electrical field, and pressing the point through the pericardium while the energy conductor is energized. The dilator device includes a handle, a dilator shaft, and an energy conductor in electrical communication with the dilator shaft. The energy conductor is configured for attachment to an external energy source. A proximal end of the dilator shaft is coupled to the handle. The dilator shaft includes a distal tip portion that tapers to a point that is smaller than a diameter of the dilator shaft.

Such a method of puncturing a pericardium may optionally include one or more of the following features. The energy conductor may be energized with direct current energy. The energy conductor may be energized with radio frequency energy. The energy conductor may be energized with cryo-energy, ultrasonic energy including multiple harmonics, direct current electroporative energy, and electrocautery.

In another implementation, a selectively flexible sheath includes a first elongate sheath that defines a first lumen, a second elongate sheath that defines a second lumen (the first elongate sheath may be at least partially disposed within the second lumen), and an inflatable member disposed within the second lumen and between the first elongate sheath and the second elongate sheath.

Such a selectively flexible sheath may optionally include one or more of the following features. While the inflatable member is deflated, the first elongate sheath may be movable in relation to the second elongate sheath. While the inflatable member is inflated, at least a portion of the first elongate sheath may be detained in a fixed relationship with at least a portion of the second elongate sheath.

In another implementation, a sheath device includes an elongate member defining a lumen, and an inflatable member disposed at a distal-most end portion of the elongate member.

Such a sheath device may optionally include one or more of the following features. While the inflatable member is deflated, an outer diameter of the inflatable member may be equal to or less than an outer diameter of the elongate member. While the inflatable member is inflated, an outer diameter of the inflatable member may be greater than an outer diameter of the elongate member. The sheath device may also include one or more electrodes disposed on the inflatable member.

In another implementation, a pericardium slitting device includes a first portion, a second portion that is coupleable to the first portion, and a cutting edge disposed between the first portion and the second portion while the first portion is coupled with the second portion.

In another implementation, a method of slitting a pericardium includes: (a) positioning a first portion of a pericardium slitting device on a first surface of the pericardium; (b) positioning a second portion of a pericardium slitting device on a second surface of the pericardium that is opposite of the first surface of the pericardium; (c) coupling the first portion with the second portion, wherein a cutting edge is disposed between the first portion and the second portion while the first portion is coupled with the second portion; and (d) pulling the coupled first and second portions such that the cutting edge cuts at least a portion of the pericardium.

In another implementation a minimally invasive pericardium shearing device includes an actuator handle configured for hand operation by a clinician, an elongate shaft extending from the actuator handle, and a distal end effector at the distal end of the elongate shaft. The distal end effector includes a lower jaw, a lower jaw extension member movably coupled with the lower jaw, and an upper jaw. The lower jaw extension member is retractable between an extended configuration in which the lower jaw extension member extends distally beyond the lower jaw and a retracted configuration in which the lower jaw extension member is retracted proximally towards the lower jaw in comparison to the extended configuration. The upper jaw is pivotable in relation to the lower jaw between an open configuration and a closed configuration in which the upper jaw and the lower jaw are approximated with each other. Pivoting the upper jaw and the lower jaw towards the closed configuration creates a shearing action therebetween.

Such a minimally invasive pericardium shearing device may optionally include one or more of the following features as sole features or in combination thereof. In addition, some embodiments may incorporate the use of such features in multiple, various sequences. The lower jaw may include a lower jaw lumen for slidably receiving a guidewire. The lower jaw extension member may include an extension member lumen for slidably receiving the guidewire. The upper jaw and the lower jaw may both include lumens for passing a liquid dye therethrough. The device may also include one or more electrodes attached to either the lower jaw or the upper jaw or both. The lower jaw extension member may be spring-biased to be in the extended configuration, or in the closed configuration. The lower jaw extension member may be controllable between the extended configuration and the retracted configuration from the actuator handle.

In another implementation, a minimally invasive pericardium shearing device includes a catheter shaft defining a lumen therethrough (the lumen configured for slidably receiving a guidewire therein), a blade member, and a distal tip protector that is selectively deployable from the distal tip. The blade member is movably coupled to the catheter shaft between a retracted configuration and a deployed configuration. The blade member includes a distal tip configured for puncturing pericardial tissue. The blade member includes a cutting edge. In the deployed configuration, the distal tip is farther away from the catheter shaft in comparison to the distal tip in the retracted configuration. The distal tip protector is configured to inhibit contact between the distal tip and tissue surfaces within the body.

Such a minimally invasive pericardium shearing device may optionally include one or more of the following features. The blade member may be pivotably coupled to the catheter shaft. The distal tip protector may comprise a wire. The distal tip protector may comprise an inflatable member. The distal tip protector may comprise a spring, coil, or gelatinous material. The device may also include one or more electrodes attached to the blade member. The distal protector can also be retractable. The distal protector can be moveable and slidable across the elongate shaft. The distal protector can also serve as a capturing device of pericardium for disposal from the body.

In another implementation, a minimally invasive pericardium shearing system includes a clamp device and an over-sheath defining an over-sheath lumen therethrough. The clamp device includes a catheter shaft defining a catheter shaft lumen therethrough (the catheter shaft lumen configured for slidably receiving a guidewire therein) and a clamp member. The clamp member is movably coupled to the catheter shaft between a retracted configuration and a clamping configuration. The clamp member includes a distal tip configured for puncturing pericardial tissue. The clamp member includes a clamp surface. In the deployed configuration, the distal tip is farther away from the catheter shaft in comparison to the distal tip in the clamping configuration. The over-sheath lumen is configured for slidably receiving the catheter shaft therein. The over-sheath includes a pericardium cutting portion on the distal end of the over-sheath. The over-sheath may include a suction or vacuum functionality for removal of pericardium from the body.

Particular embodiments of the subject matter described in this document can be implemented to realize one or more of the following advantages. Heart conditions such as, but not limited to, diastolic heart failure and others can be treated using the devices and methods provided herein. In some embodiments, the devices provided herein are configured to reduce the potential for inflicting trauma to the epicardium phrenic nerve, lungs, or any mediastinal structure. In some embodiments, the devices provided herein can deliver direct current energy to electroporate the visceral pericardium to thereby advantageously relieve pressure on the heart. In some embodiments, various heart conditions can be treated in a minimally invasive fashion using the devices and methods provided herein. Such minimally invasive techniques can reduce recovery times, patient discomfort, and treatment costs.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

FIG. 7 shows a cushion-tipped sheath within the pericardial sac in accordance with some embodiments provided herein.

FIG. 8 shows a first configuration of a distal end portion of the cushion-tipped sheath of FIG. 7.

FIG. 9 shows a second configuration of a distal end portion of the cushion-tipped sheath of FIG. 7.

FIGS. 13-15 show another example catheter-based pericardial sac slitting device.

FIGS. 16-18 show an example catheter-based pericardial resection system in accordance with some embodiments.

Like reference numbers represent corresponding parts throughout.

DETAILED DESCRIPTION

Figure 1:
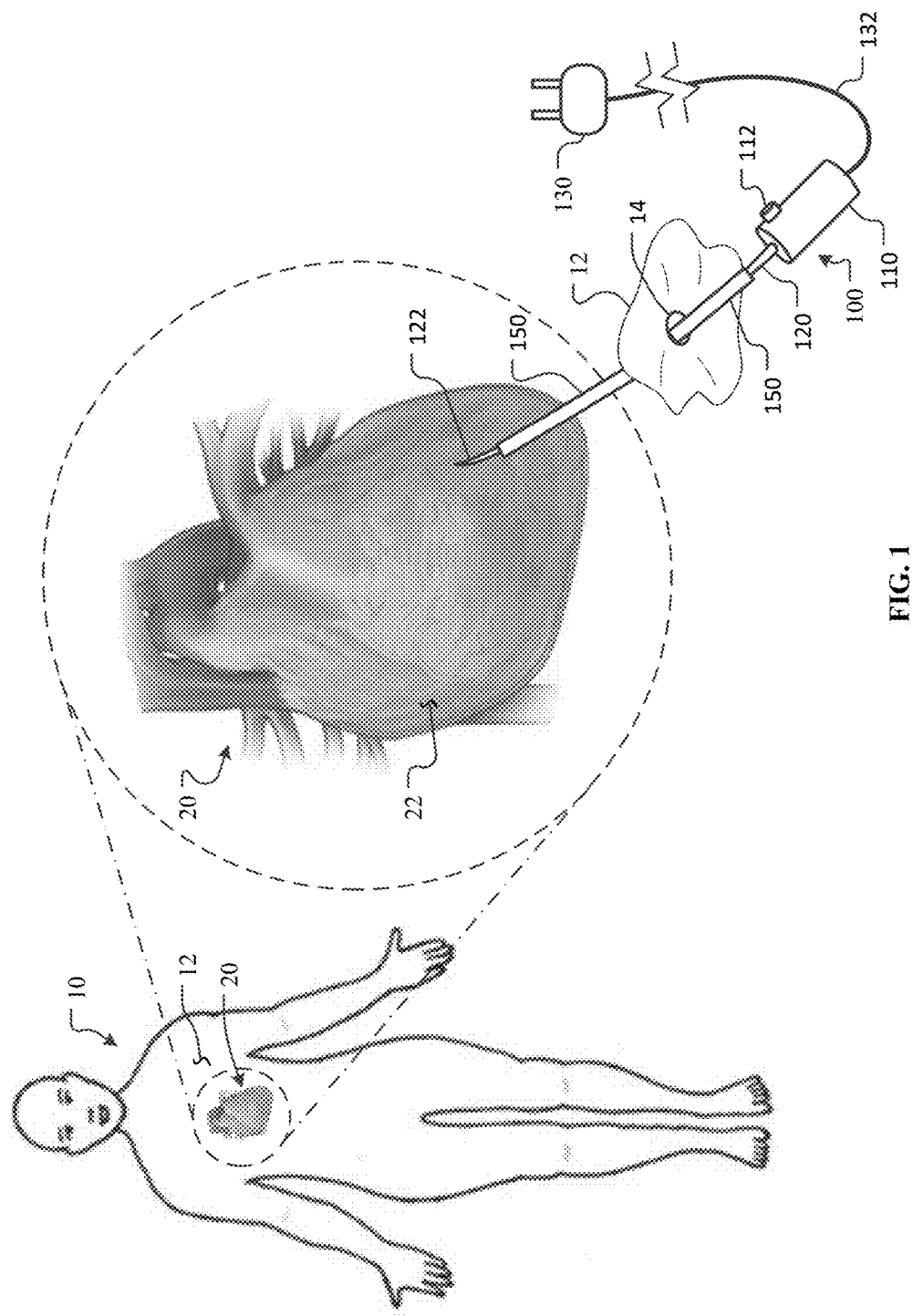
FIG. 1 is a schematic diagram of patient undergoing a percutaneous pericardial sac puncture procedure using an exemplary catheter-based dilator device in accordance with some embodiments provided herein.

This document provides devices and methods for the treatment of heart conditions. For example, this document provides devices and methods for treating heart failure with preserved ejection fraction (HFpEF), including diastolic heart failure, by performing a pericardial modification procedure. The devices and methods provided herein may also be used to treat other conditions for which pericardial modifications, including but not limited to removal of all or part of the pericardium, are advantageous. In some implementations, the devices and methods provided herein may be used to treat conditions such as increased diastolic ventricular interaction, pulmonary arterial hypertension, and right ventricular myocardial infarction, to provide some additional examples.

The devices and methods provided herein can also be used to treat pericardium disorders (e.g., pericarditis, pericardial effusion, pericardial constriction, pericardial masses, etc.). In addition, the devices and methods provided herein can also be used on pericardial sacs that are themselves healthy—so as to treat other related conditions, such as HFpEF, including diastolic heart failure.

As used within this document, the term "parietal pericardium," when used in the context of incising, dilating, removing, or otherwise modifying all or portions thereof, is defined to include a corresponding portion of fibrous pericardium. For example, the removal of a strip of parietal pericardium by definition also includes the removal of a corresponding strip of fibrous pericardium.

In some embodiments using devices and methods provided herein, HFpEF is treated by performing a full pericardectomy. In some embodiments, the treatment performed is a partial pericardectomy. In some embodiments, no pericardial tissue is removed, but the pericardial tissue is stretched, dilated, modulated or otherwise modified in such a way as to remove the constrictive force and restraint of the pericardial sac on the heart. For example, in some embodiments, a strip of the parietal pericardium is removed by cutting, tearing, slitting, expanding, cauterizing, heating, cooling, electroporating, and the like. In some embodiments, holes or tears are made in the pericardial sac, thereby facilitating dilation of the pericardium. In some embodiments the pericardial sac is slit, expanded, torn, cauterized, cut, or in some other fashion modulated or modified, to remove the constrictive force of the pericardial sac on the heart.

In some embodiments, only the outer parietal pericardium is modified, modulated, or fully or partially removed. In some embodiments, both the parietal and the visceral layers of pericardium are modified, modulated, or fully or partially removed. In some embodiments, the parietal layer is fully removed and the visceral layer is modified, modulated, or partially removed.

In some cases, the visceral layer of pericardium can be modified, modulated, or fully or partially removed with or without modifying, modulating, or fully or partially removing the outer parietal pericardium. For example, the visceral layer of pericardium can be modified or modulated by using DC/RF to soften the visceral layer.

In some embodiments, the phrenic nerves are detached from the parietal pericardium as part of the pericardial modification procedure. In some embodiments, the phrenic nerves are left attached to a portion of the parietal pericardium that is left remaining on the heart while other portions of the parietal pericardium are removed.

The devices and methods for pericardial modification provided herein encompass a range of surgical devices and techniques. In some embodiments, the pericardial modification is performed percutaneously. The approach can be, for example, subxiphoidal or lateral or via thoracotomy. In some cases it may be possible to perform the procedure by entering the heart and puncturing out of the heart through a myocardial wall (e.g. ventricle, atrium, appendage, etc.) to gain access to the pericardial space (e.g., an inside-out approach). In some embodiments, video-assisted thoracoscopy can be used. In some embodiments, robotic assistance can be used. In some embodiments, open-chest techniques are used. In some embodiments, a combination of such techniques are used.

In some embodiments, cutting of the pericardium is performed from the outside of the pericardium. In some embodiments, the pericardial sac is initially punctured by a device, and then the cutting is performed from within the pericardial space in a direction generally outward from heart tissue.

Devices having a variety of functional features are used to perform the pericardial modification methods provided herein. In some embodiments, the devices provided herein can include flexible catheter-based grasping devices (e.g., forceps, suction devices, retractors, cryo/cooling devices, and/or snares). In some embodiments, the devices provided herein are flexible catheter-based cutting devices (e.g., scissors, sheaths, knife, scapel, lasers, snares, cryogenic devices, and electrocautery devices). In some embodiments, the grasping and cutting devices are combined on a single catheter device. In some embodiments, the grasping and cutting devices are separate devices. In some embodiments, the catheter-based devices provided herein can install hooks, anchors, screws, staples, glue, and/or clips in a temporary manner to assist with performing the pericardectomy techniques. In some embodiments, an expandable element (e.g., a balloon, nitinol-based devices, etc.) can be used to create a working space in the pericardial sac and to protect the heart or otherwise direct the cutting instrument.

Components for visualizing, probing, and sensing the anatomy may be included with the devices provided herein. For example, in some embodiments the devices provided herein include electrode devices for stimulating or sensing the phrenic nerves. In some embodiments, the devices provided herein include an impedance measurement probe for sensing tissue or nerves. In some embodiments, the devices provided herein include a sonographic transducer such as a Doppler probe for visualizing the anatomy. In some embodiments, the devices provided herein include an optical camera for providing images of internal anatomy. In some embodiments, the devices provided herein include thoracoscopy style devices.

Other types of indirect visualization modalities may be used in conjunction with the devices and methods provided herein. For example, such indirect visualization modalities can include, but are not limited to, trans-thoracic echocardiography, trans-esophageal echocardiography (TEE), magnetic resonance imaging (MRI), fluoroscopy (e.g., with use of injected contrast agents), computed tomography, tactile "imaging," and the like, and combinations thereof. Such visualization modalities can be utilized one or more of pre-procedurally, intra-procedurally, and/or post-procedurally.

Further additional functional features are included in some embodiments of devices provided for performing the pericardial modification methods provided herein. In some embodiments, stabilization devices are included. In some embodiments, balloon devices are included. In some embodiments, opposable elements with a coupling means are included. In some such embodiments, a first element can be located within the pericardial space, a second element can be located on the exterior of the pericardium, and a coupling between the two catheters can enable them to cooperatively perform a pericardectomy procedure.

With reference to FIG. 1, a human patient 10 is depicted as undergoing a procedure using an example dilator device 100. Patient 10 has a skin surface 12 with a skin penetration point 14, and a heart 20 that is encompassed by a pericardium 22.

Example dilator device 100 includes a handle 110, a dilator shaft 120, and a energy source connector 130. Dilator shaft 120 extends distally from handle 110. Connector 130 is coupled to handle 110 via a cable 132. Handle 110 includes an energy actuation switch 112. Dilator shaft 120 includes a pointed distal tip portion 122.

In the depicted embodiment, example dilator device 100 is a catheter-based device configured for percutaneous functionality. That is, dilator device 100 is insertable through skin penetration point 14 (e.g., a puncture or an incision). The position of skin penetration point 14 can be, without limitation, in location such as, but not limited to the sub-xiphoidal, intercostal, and spaces such as the like.

In the depicted implementation, a delivery sheath 150 is positioned to direct the placement of dilator device 100. In some cases, an endoscope is installed in patient 10 to direct the placement of dilator device 100. In some cases, a trocar device is employed in skin penetration point 14. In some cases, a guidewire is used to direct the placement of dilator device 100. In some embodiments, dilator device 100 defines a lumen that can slidably receive a guidewire such that dilator device 100 can be installed over the guidewire, or such that a guidewire can be installed using dilator device 100 to direct the guidewire.

It should be understood that dilator device 100 can be configured for other treatment techniques and modalities in addition to the depicted configuration. For example, dilator device 100 can be configured for insertion into the vasculature of patient 10. In one such example configuration, dilator device 100 is configured for percutaneous insertion into a femoral vein or internal jugular vein to attain transvenous access to the right atrium of heart 20. In such a case, dilator device 100 can be used for puncturing the atrial septum of heart 20, for example. In another example, dilator device 100 can be configured for puncturing into heart 20 (e.g., an atrial or ventricle puncture) to access a chamber of heart 20.

While dilator device 100 is depicted as a single catheter, in some embodiments two or more catheter-based devices are used to perform the procedures provided herein. In some cases, multiple skin penetration points may be employed. Still further, in some embodiments, an open-chest procedure, or a thoracoscopy procedure can be used to perform the procedures provided herein.

In some embodiments, dilator device 100 is configured to puncture tissue. For example, in the depicted embodiment dilator device 100 is configured and arranged to puncture pericardium 22 to gain access to the pericardial space of heart 20.

Dilator device 100 can include one or more structural features that configure it to puncture tissue. For example, in some embodiments distal tip portion 122 includes a pointed distal tip. Moreover, in some such embodiments dilator device 100 can be coupled to an energy source via a connector 130. In some embodiments, the energy supplied from such an energy source can be directed to or concentrated at distal tip portion 122. With energy from an energy source located at distal tip portion 122, distal tip portion 122 can more readily puncture a tissue.

In some embodiments, a source of radio frequency (RF) energy is coupled to dilator device 100 such that RF energy is delivered to and/or concentrated at distal tip portion 122. Such RF energy can heat distal tip portion 122, and/or the tissue to which distal tip portion 122 is adjacent, to facilitate puncturing of the tissue. Alternatively, other types of energy that similarly provide a thermal action can be used in conjunction with dilator device 100. Such types of energy can include, but are not limited to, microwave, laser, ultrasound, cryoablation, chemical, high-intensity focused ultrasound (HIFU), and the like.

In some embodiments, a source of non-thermal energy is coupled to dilator device 100 such that energy is delivered to and/or concentrated at distal tip portion 122. For example, in some embodiments direct current (DC) energy is supplied to dilator device 100 such that the DC energy can be delivered from distal tip portion 122 to the tissue to be punctured. Such DC energy can facilitate electroporation of the cells of the tissue to promote a puncture of the tissue by distal tip portion 122.

In some embodiments, one or more electrodes or other types of devices (depending on the type of energy to be delivered) are located at distal tip portion 122. For example, in some embodiments distal tip portion 122 may have one or more RF and/or DC electrodes affixed to distal tip portion 122.

In some embodiments, energy is concentrated at distal tip portion 122 without having electrodes located at distal tip portion 122. In some such embodiments, the dilator device 100 includes a pointed distal tip portion 122 that naturally serves to concentrate the energy such that the energy has a higher charge density (electric field) at the pointed region of distal tip portion 122. In some embodiments, distal tip portion 122 has one or more electrodes and is additionally pointed to concentrate energy at the pointed tip.

In some embodiments, one or more portions of dilator device 100 has dielectric properties. In some embodiments, the entire dilator device 100 has dielectric properties. By exhibiting such dielectric properties, dilator device 100 can be configured such that an electrical charge (AC or DC) can be concentrated at a pointed distal tip portion 122. In some embodiments, dilator device 100 is made partially or entirely from one or more materials having dielectric properties such as, but not limited to, carbon, graphene, plastics, metal oxides, NuMetal, and the like, and combinations thereof. In some embodiments, a coating of one or more materials having dielectric properties is applied to dilator device 100.

Figure 2:
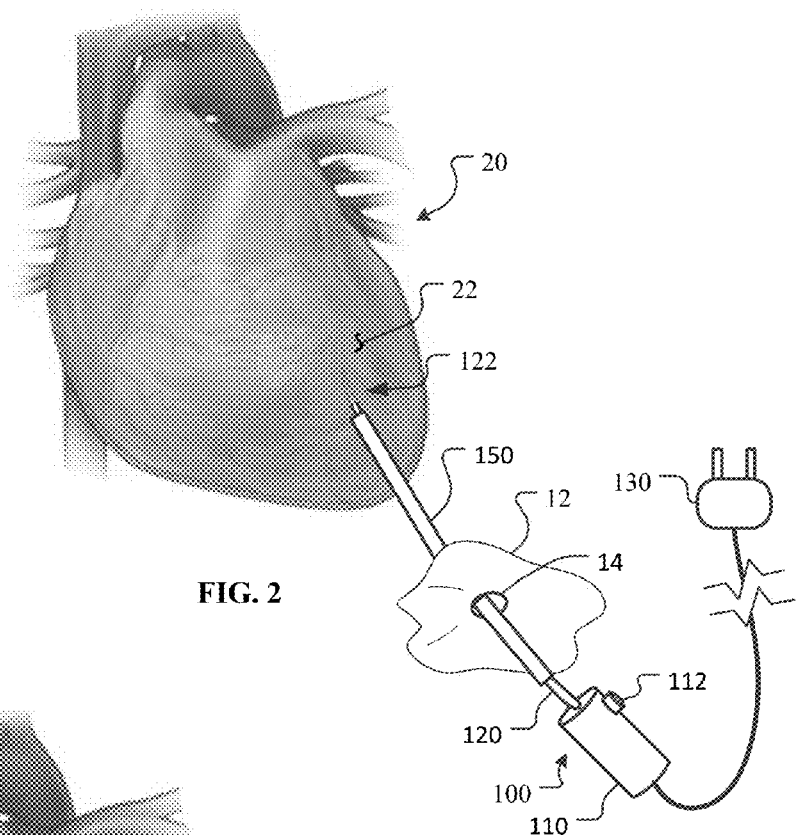
FIG. 2 shows the catheter-based dilator device of FIG. 1 after the puncture of the pericardial sac such that a distal end portion of the dilator device is positioned within the pericardial sac.
Figure 3:
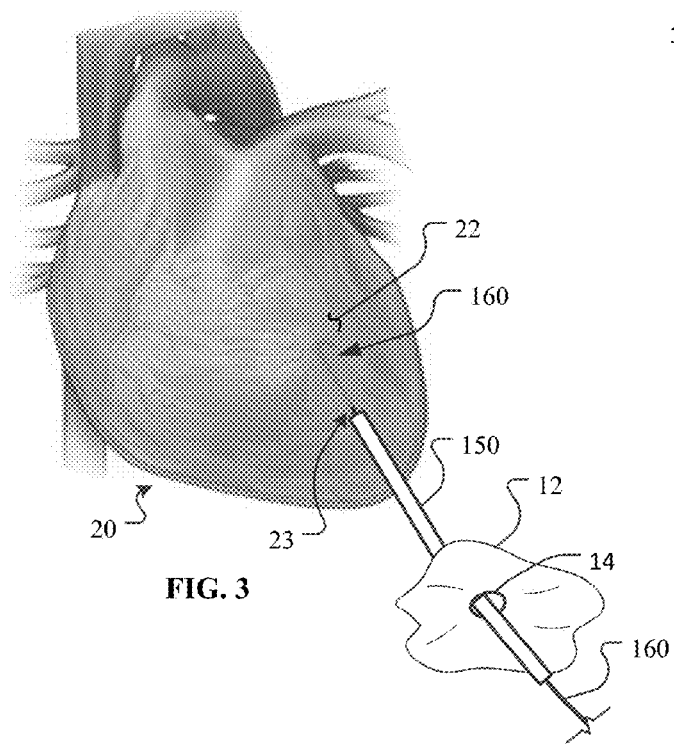
FIG. 3 shows a guidewire that has been placed within the pericardial sac using the guidance of the dilator device of FIGS. 1 and 2.

Referring also to FIGS. 2 and 3, dilator device 100 can be used to puncture pericardium 22 to provide access to the pericardial sac of heart 20. As described above, in some embodiments a clinician can activate energy activation switch 112 to deliver energy (thermal, non-thermal, etc.) to distal tip portion 122. Such energy can serve to facilitate a puncture of pericardium 22 by distal tip portion 122. As depicted in FIG. 2, the clinician can advance distal tip portion 122 into the pericardial sac after pericardium 22 is punctured by dilator device 100.

With at least a distal portion of distal tip portion 122 within the pericardial sac, in some embodiments a guidewire 160 can be advanced, via a lumen of dilator device 100 into the pericardial sac of heart 20. One example of the resulting configuration is shown in FIG. 3.

Figure 4:
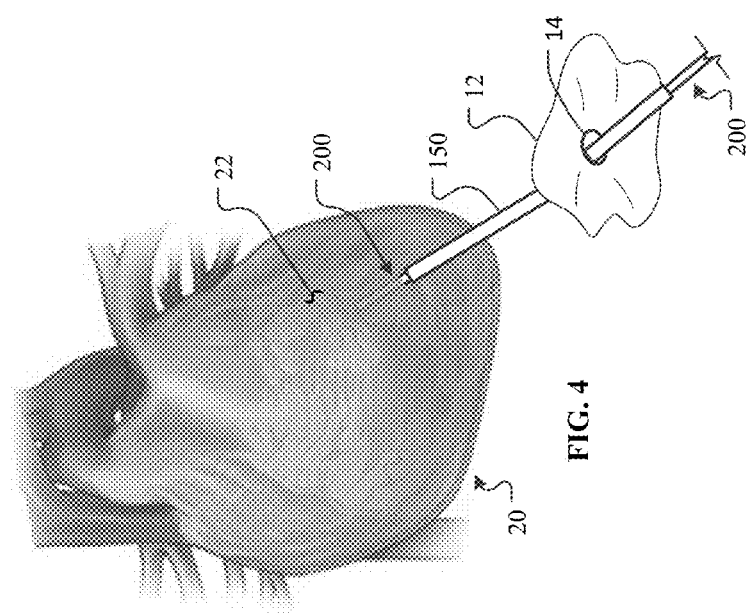
FIG. 4 shows a selectively flexible sheath within the pericardial sac in accordance with some embodiments provided herein.

Referring to FIG. 4, in some cases after access to the pericardial space of heart 20 is attained, a selectively flexible sheath device 200 in accordance with some embodiments provided herein can be inserted into the pericardial space. In one non-limiting example, selectively flexible sheath device 200 is inserted via delivery sheath 150 and delivery sheath 150 can thereafter be removed if so desired. Selectively flexible sheath device 200 can thereby provide a channel through which various types of devices can be introduced into the pericardial space of heart 20.

In some embodiments, selectively flexible sheath device 200 is configured to have a selectively adjustable flexibility and/or softness, and steerability. Such a feature can be advantageous because while manipulating selectively flexible sheath device 200 into a desired position/orientation (e.g., over a wire), flexibility and softness is desired. Such flexibility and softness can serve to prevent or reduce the propensity of causing trauma to heart 20, as well as to enhance ease of placement. When selectively flexible sheath device 200 is in a desired position/orientation, then selectively flexible sheath device 200, or portions thereof, can be stiffened, as desired, to facilitate delivery of treatment to heart 20 by one or more other devices (e.g., ablation, pericardectomy, etc.).

Figure 5:
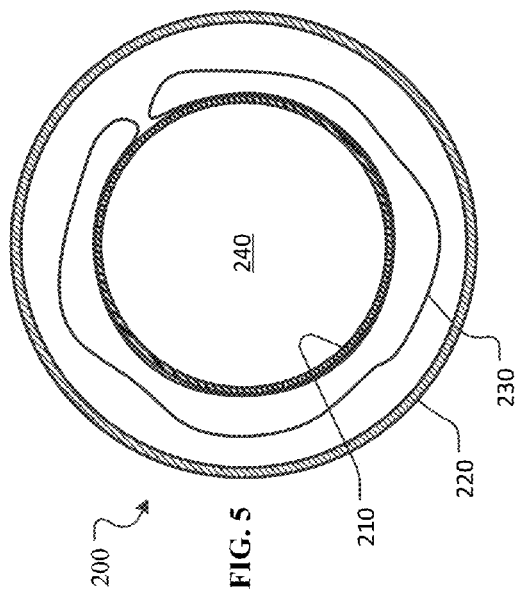
FIG. 5 shows a first cross-sectional view of the selectively flexible sheath of FIG. 4.
Figure 6:
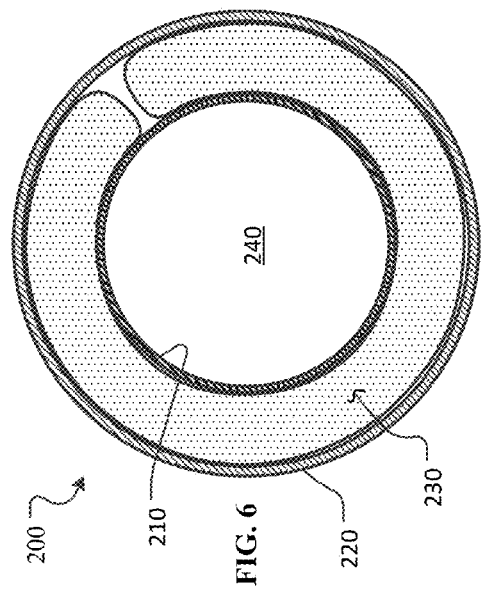
FIG. 6 shows a second cross-sectional view of the selectively flexible sheath of FIG. 4.

Referring also to FIGS. 5 and 6, a cross-sectional view of selectively flexible sheath device 200 can illustrate that, in some embodiments, selectively flexible sheath device 200 includes an inner sheath 210 surrounded by an outer sheath 220, and one or more inflatable members 230 disposed between the inner and outer sheaths 210 and 220. In some embodiments (such as the depicted embodiment), one or more inflatable members 230 are attached to inner sheath 210 and not to outer sheath 220. In some embodiments, one or more inflatable members 230 are attached to outer sheath 220 and not to inner sheath 210. In some embodiments, one or more inflatable members 230 are attached to inner sheath 210 and to outer sheath 220.

Inner and outer sheaths 210 and 220 are individually soft and flexible. When inner and outer sheaths 210 and 220 are coupled together by inflation of one or more inflatable members 230, selectively flexible sheath device 200 becomes stiffer than the individual inner and outer sheaths 210 and 220. Hence, by selectively inflating one or more inflatable members 230 a clinician can advantageously control the stiffness of selectively flexible sheath device 200 as desired.

An inner lumen 240 is defined by inner sheath 210. Inner lumen 240 provides a channel through which various types of devices can be introduced into the pericardial space of heart 20 (and into other desired locations using selectively flexible sheath device 200).

In the configuration of FIG. 5, inflatable member 230 is deflated. In the configuration of FIG. 6, inflatable member 230 is inflated. When inflatable member 230 is fully deflated, selectively flexible sheath device 200 can exhibit maximum flexibility and softness. When inflatable member 230 is fully inflated, selectively flexible sheath device 200 can exhibit maximum stiffness. When inflatable member 230 is partially inflated (e.g., to various extents), selectively flexible sheath device 200 can exhibit a range of stiffnesses between the maximum flexibility and maximum stiffness.

In some embodiments, inflatable member 230 is inflated using a gaseous inflation medium. In some embodiments, inflatable member 230 is inflated using a liquid inflation medium. The use of a liquid inflation medium will result in a greater stiffness than the use of a gaseous inflation medium. The clinician user can select the best inflation medium in accordance with the desired increase in stiffness resulting from inflation of inflatable member 230.

While in the depicted embodiment inner and outer sheaths 210 and 220 are generally coaxial when inflatable member 230 is inflated, such an arrangement is not required in all embodiments. That is, in some embodiments inflatable member 230 is disposed in only a portion of the space between inner and outer sheaths 210 and 220 such that when inflatable member 230 is expanded inner sheath 210 is biased into contact with outer sheath 220 (i.e., not coaxial).

One of skill in the art will recognize that two or more inflatable members 230 can be positioned at various locations longitudinally along selectively flexible sheath device 200. The two or more inflatable members 230 may be positioned to generally abut each other, or be positioned out of contact with each other with space therebetween. Hence, various zones along selectively flexible sheath device 200 can be selectively stiffenable as desired.

Referring to FIG. 7, in some cases after access to the pericardial space of heart 20 is attained, an atraumatically-tipped sheath device 300 in accordance with some embodiments provided herein can be inserted into the pericardial space. In one non-limiting example, atraumatically-tipped sheath device 300 is inserted via delivery sheath 150 and delivery sheath 150 can thereafter be removed if so desired. Atraumatically-tipped sheath device 300 can thereby provide a channel through which various types of devices can be introduced into the pericardial space of heart 20.

In some embodiments, atraumatically-tipped sheath device 300 is configured to have a selectively adjustable soft tip portion. Such a feature can be advantageous because while manipulating atraumatically-tipped sheath device 300 into a desired position/orientation (e.g., over a wire), an atraumatic tip is desirable. Such an atraumatic tip can serve to prevent or reduce the propensity of causing trauma to heart 20, as well as to enhance ease of placement.

Referring also to FIG. 8, in some embodiments the distal end portion of atraumatically-tipped sheath device 300 includes an inflatable member 320 that is attached to a sheath 310. It should be understood that one or more inflation lumens can be defined within a wall of sheath 310 and configured in fluid communication with inflatable member 320.

In some cases, after (or before) the distal end portion of atraumatically-tipped sheath device 300 has been inserted through an opening (e.g., puncture) in pericardium 22, the clinician-user can inflate inflatable member 320. With inflatable member 320 at least partially inflated, inflatable member 320 serves as a soft cushion such that manipulation of atraumatically-tipped sheath device 300 within the pericardial sac can be performed with a lessened risk of inducing trauma to the tissues of heart 20.

In some embodiments, when inflatable member 320 is inflated the outer diameter of inflatable member 320 is essentially equal to the outer diameter of sheath 310. In some embodiments, when inflatable member 320 is inflated the outer diameter of inflatable member 320 is larger than the outer diameter of sheath 310. In such a case, inflation of inflatable member 320 may advantageously create an additional working space within the pericardial sac.

In some embodiments, when inflatable member 320 is inflated a portion of inflatable member 320 extends distally beyond the distal-most end of sheath 310. In some embodiments, when inflatable member 320 is inflated, inflatable member 320 extends distally essentially flush with the distal-most end of sheath 310.

In some embodiments, two or more inflatable members 320 are attached to sheath 310. In some embodiments, inflatable member 320 is more longitudinally elongated than the depiction of FIG. 8.

Referring to FIG. 9, one or more electrodes 322 can be included on or in inflatable member 320. In some such embodiments, electrodes 322 can be activated for various advantageous purposes including to, but not limited to, facilitate electroporation of the visceral pericardium.

Figure 10:
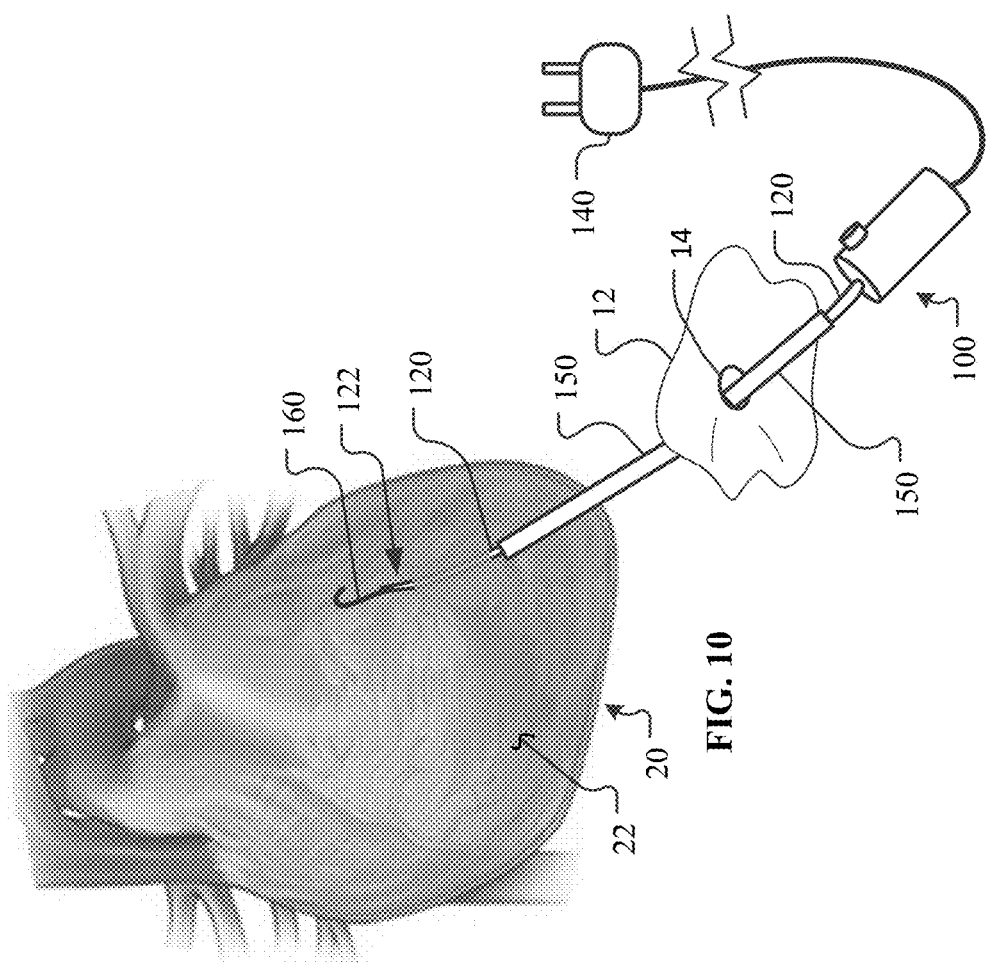
FIG. 10 shows the catheter-based dilator device of FIG. 1 after a second puncture of the pericardial sac such that a distal end portion of the dilator device is protruding from the pericardial sac.
Figure 11:
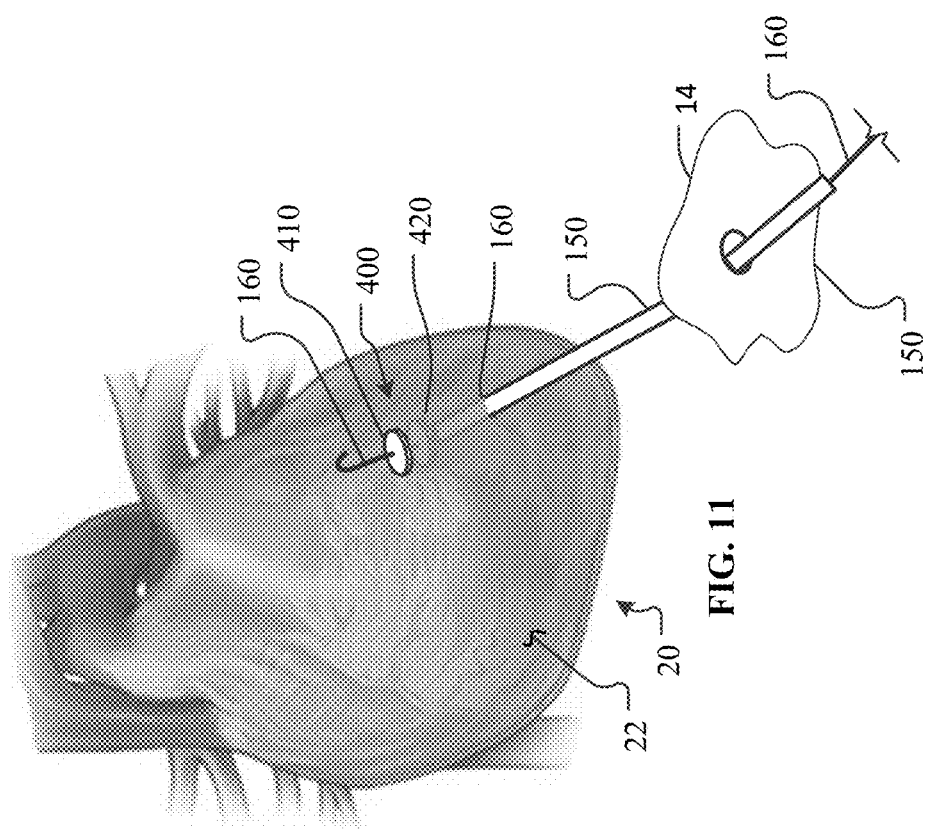
FIG. 11 shows an example catheter-based pericardial sac slitting device positioned such that a portion of the pericardium can be slit open by pulling back the slitting device.

Referring to FIGS. 10 and 11, in some implementations using example dilator device 100 a first puncture made into the pericardial sac through pericardium 22 may be followed by a second puncture made out of the pericardial sac through pericardium 22. In such an implementation, distal tip portion 122 may project out of the pericardial sac as shown in FIG. 10. In some embodiments, a guidewire 160 can be installed through a lumen of dilator shaft 120 such that a portion of guidewire 160 passes through the pericardial sac and a distal end portion of guidewire 160 projects out of the pericardial sac. Thereafter, in some implementations dilator device 100 can thereafter be withdrawn, while guidewire 160 remains as shown in FIG. 11.

A pericardium slitter device 400 can be coupled to guidewire 160. Pericardium slitter device 400 includes a first portion 410 and a second portion 420. An edge that can slit pericardium 22 is located between first portion 410 and second portion 420.

As shown in FIG. 11, to use pericardium slitter device 400, first portion 410 is positioned outside of the pericardial sac and second portion 420 is positioned inside of the pericardial sac. In other words, pericardium 22 is disposed between first portion 410 and second portion 420. The edge that can slit pericardium 22 is thereby in contact with pericardium 22.

In some embodiments, first portion 410 and second portion 420 lock together with pericardium 22 sandwiched therebetween. In some embodiments, first portion 410 and second portion 420 are compressed together with pericardium 22 sandwiched therebetween by pulling on guidewire 160 and simultaneously pushing on (i.e., providing backpressure via) sheath 150 which is in contact with second portion 420.

With first portion 410 and second portion 420 locked or otherwise held together, guidewire 160 can be pulled proximally to pull first portion 410 and second portion 420 proximally. In doing so, the edge between first portion 410 and second portion 420 can slit pericardium 22 such that the pericardial sac becomes slit opened.

In some embodiments, first portion 410 and/or second portion 420 have one or more ports through which a contrast agent can be emitted to help with visualization of the process of using pericardium slitter device 400.

Figure 12:
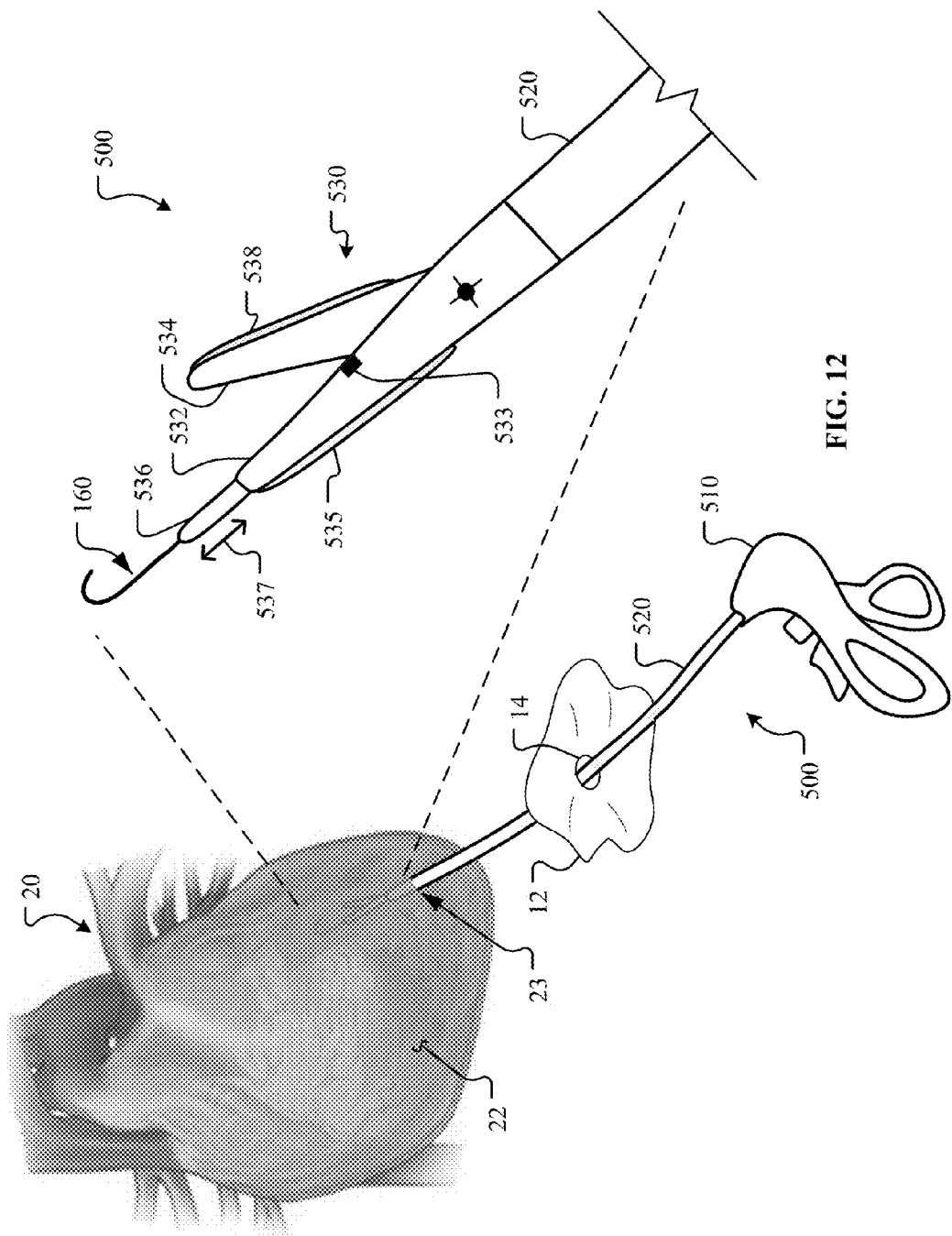
FIG. 12 shows another example catheter-based pericardial sac slitting device.

Referring to FIG. 12, another example pericardium slitter device 500 can be used to sever the pericardium 22. Pericardium slitter device 500 can be installed over guidewire 160. That is, in some cases prior to placing pericardium slitter device 500 into position for severing pericardium 22, guidewire 160 is installed (e.g., as per FIG. 3) through a pericardial opening 23. Then, pericardium slitter device 500 is advanced over guidewire 160, through skin penetration point 14 and pericardial opening 23, such that a distal end portion of pericardium slitter device 500 is positioned within the pericardial space (between the visceral and parietal layers of pericardium 22).

In some embodiments, pericardium slitter device 500 includes a control handle 510, a shaft 520, and a distal end effector 530. Shaft 520 extends between control handle 510 and distal end effector 530. Control handle 510 is configured to actuate one or more actuatable elements of distal end effector 530.

In the depicted embodiment, distal end effector 530 (see magnified view of FIG. 12) include a lower jaw 532, and upper jaw 534, and a lower jaw extension 536. Upper jaw 534 and lower jaw 532 are pivotable in relation to each other, and are compatibly configured for shearing or severing tissue between cutting edges of upper jaw 534 and lower jaw 532. That is, like a scissors, upper jaw 534 and lower jaw 532 can be pivoted in relation to each other, and tissue positioned between upper jaw 534 and lower jaw 532 can be thereby sheared. In some embodiments, the distal tips of upper jaw 534 and lower jaw 532 are blunt, atraumatic tips. In particular embodiments, two or more distal end effectors 530 are included in a single pericardium slitter device 500. In some such cases, the two or more distal end effectors 530 are disposed laterally side-by-side. The two or more distal end effectors 530 may be actuated individually or jointly.

As stated above, pericardium slitter device 500 is configured to be advanced over guidewire 160. More particularly, in the depicted embodiment lower jaw 532 and lower jaw extension 536 define lumens that slidably receive guidewire 160.

In the depicted embodiment, lower jaw extension 536 retractably extends from lower jaw 532. That is, lower jaw extension 536 is configured to extend and retract from lower jaw 532 as indicated by arrow 537.

In some embodiments, lower jaw extension 536 can retract substantially completely within lower jaw 532. In that configuration, the tips of lower jaw 532 and upper jaw 534 are essentially approximated with each other while lower jaw 532 and upper jaw 534 are closed in relation to each other.

While lower jaw extension 536 is extending from lower jaw 532 (e.g., as depicted), lower jaw extension 536 effectively increases the length of lower jaw 532. This arrangement provides various advantages as described further below.

In some embodiments, the extension and retraction of lower jaw extension 536 is controllable from control handle 510. That is, in some embodiments control handle 510 includes one or more actuators that can be used by a clinician operator to extend and/or retract lower jaw extension 536 in relation to lower jaw 532 as desired.

In some embodiments, lower jaw extension 536 is spring-biased to be in the extended configuration in relation to lower jaw 532. In such a case, when lower jaw extension 536 is physically forced towards lower jaw 532, the spring force will be overcome and lower jaw extension 536 will be retracted at least partially within lower jaw 532.

In some cases, pericardium slitter device 500 can be deployed and operated as follows. While pericardium slitter device 500 is being advanced over guidewire 160, upper jaw 534 and lower jaw 532 are closed in relation to each other (i.e., jaws 532 and 534 are approximated). Distal end effector 530 enters the pericardial space through pericardial opening 23 while upper jaw 534 and lower jaw 532 are closed. Lower jaw extension 536 can be either retracted or extended while pericardium slitter device 500 is advanced over guidewire 160 into the pericardial space.

If lower jaw extension 536 was not extended while pericardium slitter device 500 was advanced over guidewire 160, then, after distal end effector 530 has entered the pericardial space, lower jaw extension 536 is deployed to an extended orientation in relation to lower jaw 532. After distal end effector 530 has entered the pericardial space, the jaws 532 and 534 are actuated to become at least partially open in relation to each other (this is done while distal end effector 530 is in the pericardial space).

Next, pericardium slitter device 500 is pulled back (proximally) in relation to heart 20. As pericardium slitter device 500 is pulled back (by the clinician), upper jaw 534 exits from the pericardial space prior to lower jaw 532. That is the case because the extended lower jaw extension 536 effectively makes the length of lower jaw 532 longer than the length of upper jaw 534. Hence, upper jaw 534 exits from pericardial opening 23 before lower jaw 532 as pericardium slitter device 500 is being pulled back. When upper jaw 534 has exited the pericardial space, but prior to lower jaw 532 exiting from the pericardial space, the clinician stops pulling back pericardium slitter device 500. In that orientation, distal end effector 530 is oriented to begin shearing pericardium 22. That is, jaws 532 and 534 are on opposite sides of pericardium 22 such that actuating jaws 532 and 534 into the closed orientation will shear pericardium 22.

In some cases, prior to shearing pericardium 22, the clinician takes measures to identify a path on the pericardium that is free of tissue other than the pericardium. Such a path may be correspond to a single shearing action or to multiple shearing actions. For example, as described elsewhere herein, in some cases the position of other tissue(s) or structures such as, but not limited to, a phrenic nerve, a vagus nerve, lung tissue, mediastinal structures, and the like can be identified and/or eliminated from being in a particular path on the pericardium. In that fashion, the clinician can identify a path for resection and avoid damaging collateral tissue and/or structures while modifying the pericardium.

From the foregoing description, it can be appreciated that one advantage provided by the lower jaw extension 536 is to facilitate getting distal end effector 530 into a proper orientation in relation to pericardium 22 such that pericardium 22 can be sheared by distal end effector 530. That is, with lower jaw extension 536 effectively making lower jaw 532 longer than upper jaw 534, as pericardium slitter device 500 is pulled back, upper jaw 534 will exit the pericardial space while lower jaw 532 remains within the pericardial space.

In some cases, while the clinician is shearing pericardium 22, lower jaw extension 536 remains extended. In that orientation, lower jaw extension 536 can help to maintain lower jaw 532 within the pericardial space.

In some cases, the clinician may also use a device to capture and control pericardium 22 during the shearing process. By controlling pericardium 22 (e.g., applying counter-traction), a more precise pericardial modification procedure may be performed in some cases. That can be the case especially when making a second cut (and additional cuts thereafter) because free edges of pericardium 22 are created by the first cut. In some such cases, without limitation, a grasping device, or a suction or vacuum device can be used for such a purpose. Such a device can be incorporated with pericardium slitter device 500 (e.g., refer to FIGS. 22-24), or can be a separate device that may access pericardium 22 via skin penetration point 14, or through another route.

In some cases, the clinician may at least partly use or rely on tactile feedback from pericardium slitter device 500 to ascertain the position of distal end effector 530 in relation to pericardium 22. That is, in some cases the clinician can apply distally-directed force via pericardium slitter device 500 and tactilely sense when back-pressure indicates that distal end effector 530 (in the open configuration) is engaged with pericardium 22 such that pericardium slitter device 500 is positioned for a subsequent cutting action.

As the shearing of pericardium 22 continues, in some cases upper cul-de-sac areas of the pericardial space will be reached by distal end effector 530. In such a case, lower jaw extension 536 will need to be retracted in order to shear pericardium 22 essentially all the way to the location of the upper cul-de-sac areas of the pericardial space. In some embodiments, lower jaw extension 536 is spring loaded such that, when lower jaw extension 536 reaches the cul-de-sac, forces from the tissue are naturally exerted against lower jaw extension 536 to make lower jaw extension 536 retract in relation to lower jaw 532. In some embodiments, the clinician can actuate pericardium slitter device 500 to retract lower jaw extension 536 as it reaches the upper cul-de-sac areas of the pericardial space. Hence, the fact that lower jaw extension 536 can be retracted in relation to lower jaw 532 allows pericardium 22 to be sheared essentially all the way to the location of the upper cul-de-sac areas of the pericardial space. In some cases, the one or more slits in pericardium 22 are formed in pericardium 22 from an inferior point to one or more superior points. In some such cases, the inferior point is adjacent the xiphoid between the lungs and the one or more superior points are adjacent the pericardial reflection.

In some embodiments, both upper jaw 534 and lower jaw 532 include lumens through which contrast agent (radiopaque dye) can be injected for fluoroscopic visualization. These features can be used to determine whether upper jaw 534 is outside of the pericardial space and lower jaw 532 is within pericardial space (i.e., in the desired configuration for shearing pericardium 22). For example, dye can be injected via lower jaw 532 (and the dye should be within the pericardial space) and dye can non-contemporaneously be injected via upper jaw 534 (and the dye should be outside of the pericardial space). The location of the injected dye (inside and outside of the pericardial space) can be ascertained using x-ray fluoroscopy, for example. Hence, by injecting dye through lumens of both upper jaw 534 and lower jaw 532 (separately) the clinician can determine that distal end effector 530 is properly positioned for cutting pericardium 22.

In some embodiments, one or more electrodes 533 can be located on either upper jaw 534 or lower jaw 532 (or both) at or near the juncture of upper jaw 534 and lower jaw 532 (i.e., the juncture while the jaws 532 and 534 are open). For example, in some embodiments the inner angles of the cutting edge of the jaws 532 and 534 to allow for bipolar radiofrequency ablation to allow for tissue pericardial destruction in between the jaws 532 and 534. The one or more electrodes 533 can be actuated by the clinician operator of pericardium slitter device 500 to assist with the start of shearing pericardium 22 between upper jaw 534 and lower jaw 532. For example, the one or more electrodes 533 can be placed into contact with pericardium 22, the one or more electrodes 533 (supplied by RF energy, for example) can be actuated to burn a small portion of pericardium 22, and then the pivoting actuation between the jaws 532 and 534 can be actuated to shear pericardium 22 from the small, burned portion. In some embodiments, the same electrodes 533 can also have pacing and/or recording functions to ensure there is no myocardial contact and/or no phrenic nerve contact.

In some embodiments, the lower side of the lower jaw 532 (i.e., the side of lower jaw 532 that is opposite of the cutting side of lower jaw 532) is configured with an inflatable member 535. In some cases, inflatable member 535 can be deployed while lower jaw 532 is in contact with the epicardium. Accordingly, inflatable member 535 can distribute forces from lower jaw 532 over a larger area to reduce the pressure exerted by lower jaw 532 on the arteries and/or epicardium. In addition, in some cases when inflatable member 535 is inflated, additional pressure is exerted against the parietal pericardium from the lower jaw 532, which can be beneficial for the cutting action of pericardium slitter device 500.

In some embodiments, the upper side of upper jaw 534 includes an inflatable member 538 (i.e., the side of upper jaw 534 that is opposite of the cutting side of upper jaw 534). Inflatable member 538 can be deployed to make the upper side of upper jaw 534 more cushioned and more atraumatic.

Referring to FIGS. 13-15, another example pericardium slitter device 600 can be used to sever the pericardium 22 (refer to FIG. 3). Pericardium slitter device 600 can be installed over guidewire 160. That is, prior to placing pericardium slitter device 600 into position for severing pericardium 22, guidewire 160 is installed (e.g., as per FIG. 3) through a pericardial opening 23. Then, pericardium slitter device 600 is advanced over guidewire 160, through skin penetration point 14 and pericardial opening 23, such that a distal end portion of pericardium slitter device 600 is positioned within the pericardial space (between the visceral and parietal layers of pericardium 22). Pericardium slitter device 600 is configured as shown in FIG. 13 as pericardium slitter device 600 is advanced over guidewire 160.

Pericardium slitter device 600 includes a shaft 610 and a reverse-cutting blade 620. Pericardium slitter device 600 can also include a control handle (not shown) such that a clinician operator can operate and control pericardium slitter device 600.

With the distal end portion of pericardium slitter device 600 positioned within the pericardial space, reverse-cutting blade 620 can be deployed (as depicted in FIG. 14). In the depicted embodiment, blade 620 is pivotably deployable from shaft 610.

Reverse-cutting blade 620 includes a distal tip 622 and a cutting edge 624. In some embodiments, blade 620 also includes one or more electrodes 623. As reverse-cutting blade 620 is deployed to the orientation of FIG. 14, distal tip 622 can puncture through pericardium 22. In some embodiments, distal tip 622 is sharp so that it can puncture pericardium 22. In some embodiments, distal tip 622 includes an electrode to facilitate penetration through pericardium 22.

With distal tip 622 of reverse-cutting blade 620 on the outside of the pericardial space, the clinician can pull back pericardium slitter device 600 (as indicated by arrow 630) and cutting edge 624 will sever pericardium 22. In some embodiments, as depicted in FIG. 15, a distal tip protector 630 is deployable (after distal tip 622 has punctured through pericardium 22) to configure distal tip 622 as an atraumatic tip (and prior to pulling back on pericardium slitter device 600). Then, as the clinician pulls pericardium slitter device 600 back to sever pericardium 22, distal tip protector 630 reduces the potential for distal tip 622 to damage tissue surrounding the heart.

In some embodiments, such as the depicted embodiment, distal tip protector 630 is a deployable wire that naturally bundles up into a generally spherical shape as it exits through a lumen at distal tip 622. In some embodiments, distal tip protector 630 is an inflatable member. In some embodiments, distal tip protector 630 is deployable member (e.g., a cap-like member) that can be selectively deployed to protect distal tip 622 from contacting tissues.

In some embodiments, an inflatable member 612 is attached to shaft 610 on an opposite side of shaft 610 as compared to blade 620. In some cases, inflatable member 612 can be deployed while pericardium slitter device 600 is in contact with the epicardium. Accordingly, inflatable member 612 can distribute forces from shaft 610 over a larger area to reduce the pressure exerted by shaft 610 on the arteries and/or epicardium. In addition, in some cases when inflatable member 612 is inflated, additional pressure is exerted against the parietal pericardium from the shaft 610 and blade 620, which can be beneficial for the cutting action of pericardium slitter device 600.

Referring to FIGS. 16-18, an example pericardial resection system 700 can be used in to remove a portion of pericardium 22 (refer to FIG. 3). Pericardial resection system 700 includes a clamp device 710 and an over-sheath 730. Over-sheath 730 is slidably disposable over clamp device 710.

Clamp device 710 is deployable over guidewire 160 such that a distal end portion of clamp device 710 is located in the pericardial space (e.g., in accordance with techniques provided herein). Clamp device 710 includes a shaft 712 and a clamp member 720. In some embodiments, such as the depicted embodiment, clamp member 720 is pivotably deployable from shaft 712.

When the distal end portion of clamp device 710 is positioned within the pericardial space, clamp member 720 can be deployed such that a distal tip 722 of clamp member 720 penetrates through pericardium 22 (as depicted by FIG. 17). After that, clamp member 720 can be repositioned such that pericardial tissue is clamped between a clamp surface 724 of clamp member 720 and shaft 712 (as depicted by FIG. 18).

Next, a pericardium cutting device can be used slit pericardium 22 along a line that is generally parallel and spaced apart from shaft 712. For example, in some cases either pericardium slitter device 500 or pericardium slitter device 600 can be used to create the cut in the pericardium 22. Alternatively, in some cases a pericardium cutting device can be incorporated with clamp device 710.

The cutting of pericardium 22 along a line that is generally parallel and spaced apart from shaft 712 creates a free margin of pericardium 22. Then, the clamp device 710 can be rotated about its longitudinal axis to roll up pericardial tissue round shaft 712 (e.g., like a scroll or a window shade). In some cases, about 3 cm to about 4 cm of pericardial tissue is rolled up around shaft 712. In some cases, about 2 cm to about 5 cm, or about 3 cm to about 6 cm, or about 4 cm to about 8 cm of pericardial tissue is rolled up around shaft 712.

After the pericardial tissue has been rolled up around shaft 712, over-sheath 730 can be advanced distally as depicted by arrow 740 in FIG. 18. Over-sheath 730 includes a leading cutting end 732. In some embodiments, leading cutting end 732 is sharp such that it slices through pericardium 22 as over-sheath 730 is advances over clamp device 710. In some embodiments, leading cutting end 732 can include one or more electrodes that can be used to burn through pericardium 22.

Over-sheath 730 can be advanced distally such that clamp device 710 with the pericardium tissue wrapped around it becomes located within a lumen of over-sheath 730. Then, over-sheath 730 can be canted to totally shear the portion of pericardium 22 that is wrapped around the clamp device 710. Thereafter, pericardial resection system 700 can be removed from the patient. In that fashion, a portion of pericardium 22 can be resected.

In some embodiments, one or more pacing electrodes can be located on the clamp device 710 or the over-sheath 730 so during use it can be determined whether the devices are facing the heart and also know when the devices are close to the phrenic nerve.

In some embodiments, over-sheath 730 can include features for suction of tissue, air, and/or fluid (e.g., both injectable and vacuuming out). This will not only provide a means to clean the tools if they acquire too much pericardial tissue, but will also serve to remove pericardium 22 from the body.

In some embodiments, over-sheath 730 can alternatively or additionally include a second cutting surface, such as a cutting ring on or in the inner portion of over-sheath 730. Such a cutting ring would be inside (e.g., midshaft) rather than at the leading edge so as to cut within a protected sheath. This will facilitate removal of pericardial tissue from the body.

FIGS. 19A-19G are a series of illustrations depicting a pericardial modification procedure in accordance with some embodiments provided herein. The pericardial modification procedure is performed using an exemplary pericardectomy system 800 on a heart 20 that has a pericardium 22. Pericardectomy system 800 represents any of the example pericardectomy devices and systems provided herein, and/or combinations thereof. For example, while pericardectomy system 800 does not illustrate a grasping device for grasping and manipulating the pericardial tissue, one or more grasping devices may be included in some embodiments. It should also be understood that while FIGS. 19A-19F show the incision and removal of a particular portion of pericardial tissue (orientated on a particular portion of heart 20), other portions and locations of pericardial tissue can be incised and/or removed using the same or similar pericardial modification procedure techniques as illustrated here. For example, in another example implementation the pericardial tissue constraining the apex of heart 20 can be modified by, for example, by incision and/or removal (refer also to FIGS. 21A-21D for additional examples). Moreover, in some cases substantially an entirety of the pericardial tissue is removed in some cases (refer to FIG. 19 G). The pericardial modification procedure is performed while avoiding trauma to the epicardial surface of heart 20 as well as the phrenic nerves and epicardial coronary arteries.

Figure 19A:
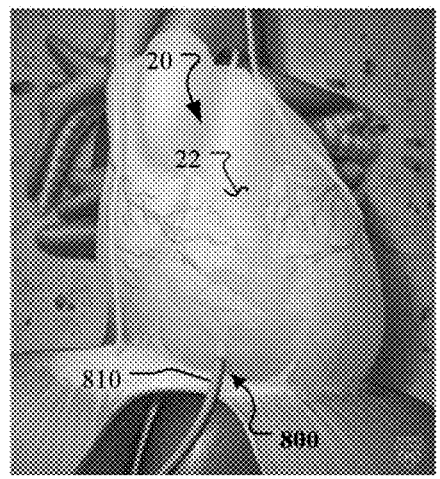
FIGS. 19A-19G are a series of illustrations depicting a pericardial modification procedure in accordance with some embodiments provided herein.

In FIG. 19A, a delivery sheath 810 of pericardectomy system 800 is shown after having been partially inserted through an incision to pericardium 22. In this orientation, the distal tip portion of delivery sheath 810 is within the pericardial sac and adjacent to the surface of heart 20.

Figure 19B:
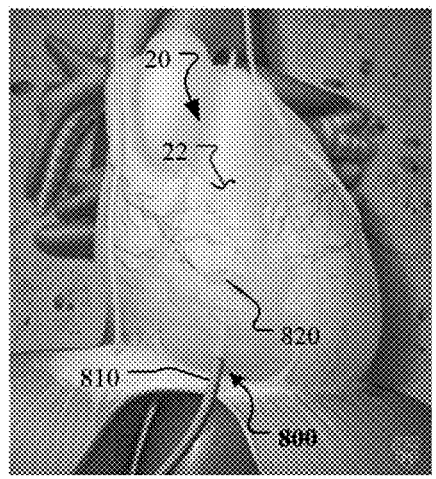

In FIG. 19B, a guidewire 820 has been advanced from sheath 810. Advancement of guidewire 820 can be performed using fluoroscopy or other imaging modalities.

Figure 19C:
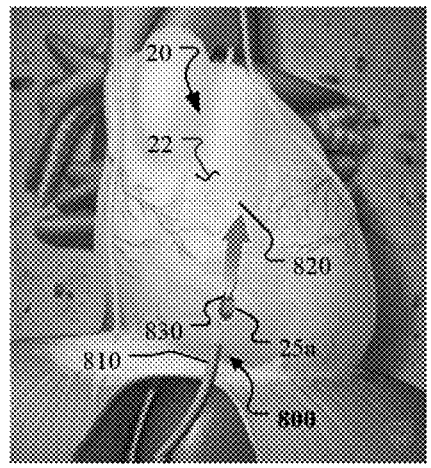
Figure 19D:
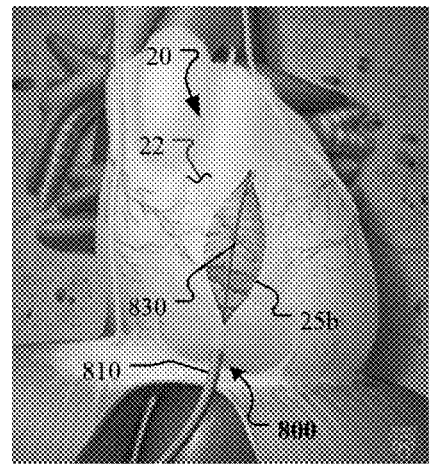

In FIGS. 19C and 19D, a pericardial modification device 830 is being advanced over guidewire 820. Pericardial modification device 830 is creating an opening 25a and 25b in pericardium 22.

Figure 19E:
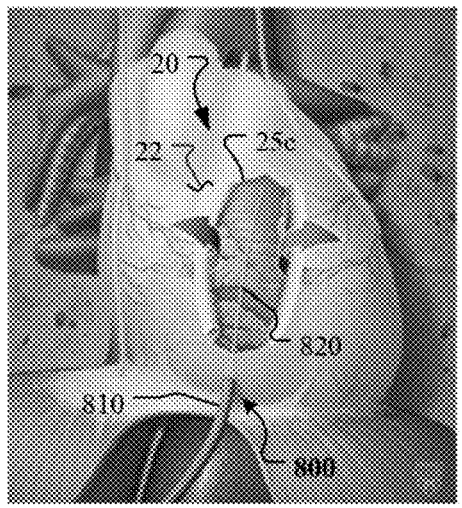
Figure 19F:
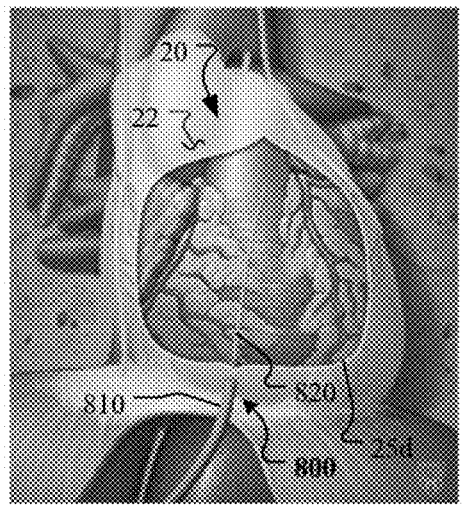

In FIGS. 19E and 19F, pericardial modification device 830 has been retracted into sheath 810. The openings 25c and 25d in pericardium 22 are enlarged as desired. In some embodiments, an additional grasping/cutting device is used to remove the pericardial tissue to arrive at the configuration shown in FIG. 19F. In some cases, the configuration shown in FIG. 19F exemplifies the final configuration resulting from the pericardectomy procedure.

Figure 19G:
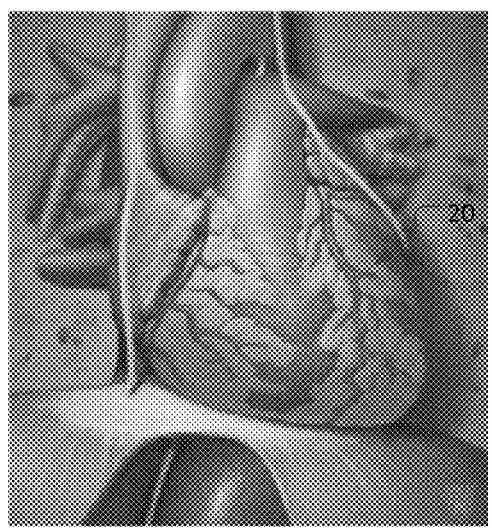

In FIG. 19G, substantially an entirety of pericardium 22 has been removed from heart 20. Hence, it should be understood that in some cases the pericardial modification procedures described herein can include: (i) incision(s) to the pericardium without removal of tissue, (ii) removal of a partial amount of pericardial tissue, (iii) removal of all pericardial tissue, and (iv) combinations thereof.

Figure 20:
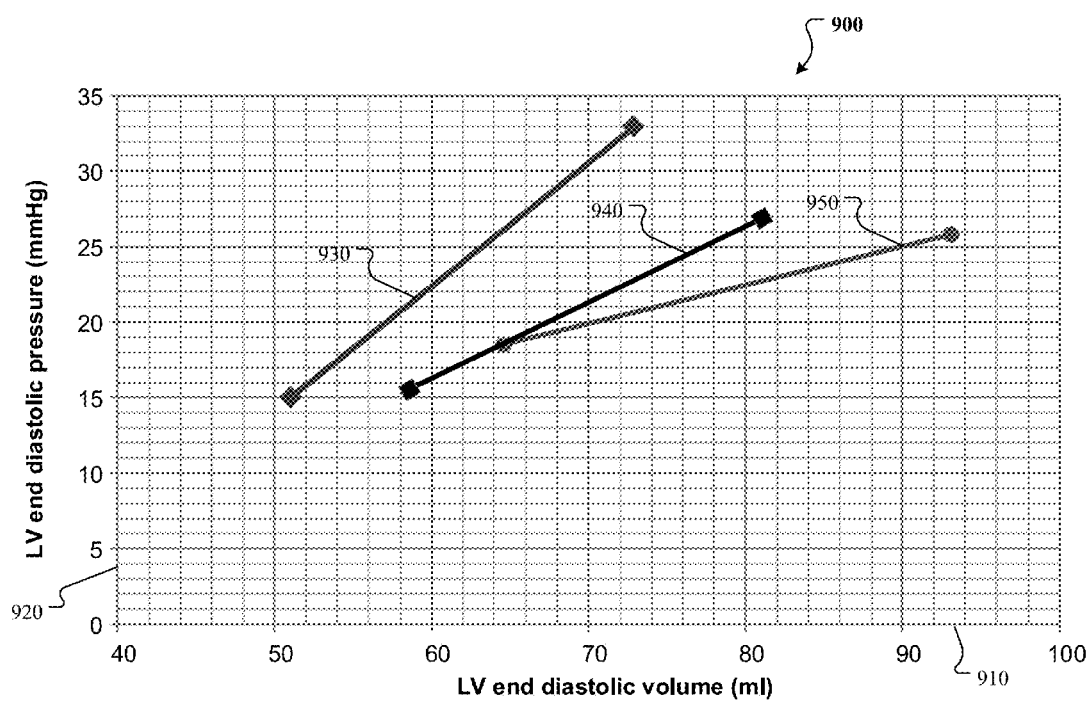
FIG. 20 is a graph that illustrates the results of a pericardial modification procedure.

With reference to FIG. 20, a graph 900 of left ventricular end diastolic volume 910 (on the x-axis) versus left ventricular end diastolic pressure 920 (on the y-axis) is provided. The lines 930, 940, and 950 are the results from acute experiments using four normal dogs. These experiments were performed to verify the acute benefits of pericardiectomy, and to explore whether a limited pericardial incision might provide similar benefit to complete pericardial resection. Left ventricular pressures and volumes were measured at baseline (the lower endpoint of each line 930, 940, and 950) and after rapid saline loading (the upper endpoint of each line 930, 940, and 950). Line 930 shows the left ventricular pressure and volume with the pericardium intact. Line 940 shows the left ventricular pressure and volume after a single linear left lateral pericardial incision. Line 950 shows the left ventricular pressure and volume after complete pericardiectomy.

It can be seen that the left ventricular diastolic pressure-volume relation shifted rightward indicating improved compliance with performance of the pericardial modification procedure techniques provided herein. A significant amount of this benefit was achieved with the single linear incision over the left lateral pericardium as represented by line 940. Note that the magnitude of increase in left ventricular filling pressures with saline bolus (700 ml) was lower from thoracotomy to pericardial incision to full pericardiectomy. There was a slight creep upward in left ventricular end diastolic pressures at the re-baseline state prior to the final saline loading (after full pericardiectomy), likely due to the additive effect of receiving multiple serial boluses to increase circulating plasma volume. Overall, the increase in left ventricular pressure per increase in left ventricular volume with saline load decreased progressively from line 930 with the pericardium intact (0.90±0.22 mmHg/ml) to line 940 with the pericardial incision (0.44±0.13, p=0.04 vs. intact) to line 950 with the full pericardiectomy (0.28±0.24, p=0.006 vs. intact, p=0.3 vs. incision).

Figure 21A:
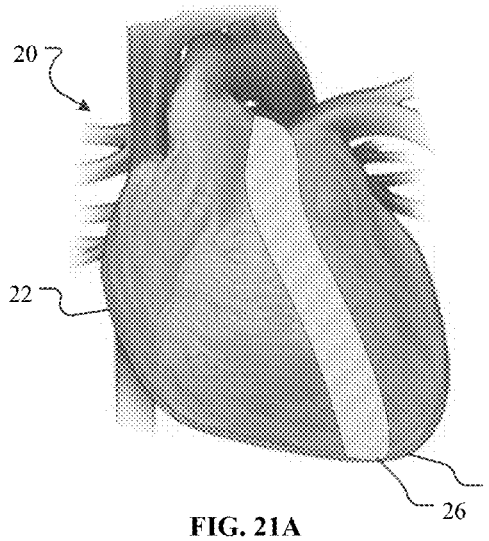
FIGS. 21A-21D are schematic illustrations of a heart after a pericardectomy in accordance with some embodiments provided herein.
Figure 21B:
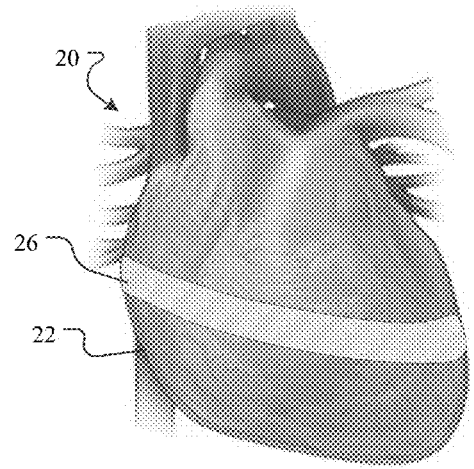

FIGS. 21A and 21B illustrate heart 20 that has had a strip 26 of pericardium 22 removed. The area of strip 26 exposes the epicardial pericardium or the heart tissue (in such cases when the epicardial pericardium has also been removed). Strip 26 of pericardium 22 has been removed using the devices and methods provided herein.

FIG. 21A depicts strip 26 running generally from the apex of heart 20 and in a generally superior/inferior direction. FIG. 21B depicts strip 26 running around the middle of heart 20, and in a generally transverse posterior/anterior direction. In some cases, strip 26 runs all the way around heart 20 (including posterior portions on heart 20 not visible in FIGS. 21A and 21B). In some cases, strip 26 runs partially around heart 20 (e.g., generally as shown, or in a shorter segment than shown). All combinations of directions and lengths of strip 26 are envisioned within the scope of this document.

Measures can be taken to inhibit or prevent the reformation of tissue (e.g., scar tissue) across strip 26. In some cases, the width of strip 26 can be made sufficiently wide to inhibit or prevent the reformation of tissue across strip 26. For example, in some cases making the width of strip 26 from about 0.5 cm to about 1 cm, or about 0.75 cm to about 2 cm or more can inhibit or prevent the reformation of tissue across strip 26. In some cases, the edges of pericardium 22 can be cauterized to inhibit or prevent the reformation of tissue across strip 26. In some cases, the cut edges of pericardium 22 can be doubled over.

In cases where portions of the parietal pericardium are removed but the visceral pericardium remains, measures can be taken to inhibit or prevent attachment of the parietal and visceral pericardial layers that might otherwise create smaller but significant pericardial spaces again, thereby causing restraint in diastole. For example, attachment of the parietal and visceral pericardial layers can be inhibited or prevented by removing a significant amount of the parietal pericardium. In such cases, strip 26 can be made wider to decrease the propensity for attachment of the parietal and visceral pericardial layers.

In some cases, one or more slits in pericardium 22 are formed in pericardium 22 from an inferior point to one or more superior points (or the reverse). In some such cases, the inferior point is adjacent the xiphoid between the lungs and the one or more superior points are adjacent the pericardial reflection.

Figure 21C:
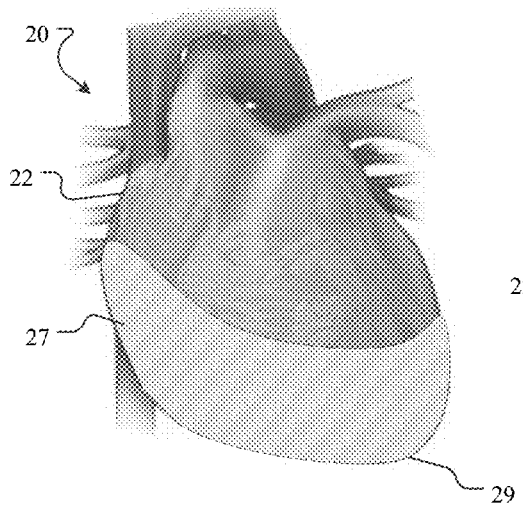

FIG. 21C illustrates another pattern for partial removal of pericardium 22. That is, pericardium from an inferior portion 27 has been removed. The removal can include only the parietal layer, or both the parietal and visceral pericardial layers of pericardium 22.

In some embodiments, the methods of performing pericardectomy provided herein can begin by removing portions of pericardium 22 near the apex 29 of heart 20. For example, a generally circular section of pericardium 22 can be removed at apex 29. In some embodiments, this technique can be used advantageously to avoid the phrenic nerves. If additional removal of pericardium 22 is desired (e.g., if additional diastolic pressure removal is desired), further removal of pericardium 22 can be propagated from the region removed at apex 29. In some embodiments, pericardium 22 covering the left and right ventricles, or substantial portions thereof, are removed.

Figure 21D:
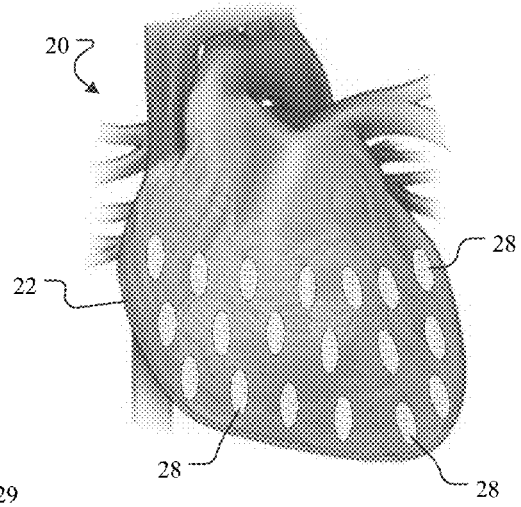

FIG. 21D illustrates another pattern for partial removal of pericardium 22. The pattern is made by creating multiple incisions, tears, or removals of pericardium 22 to create the multiple openings 28. This pattern can allow the volume contained by pericardium 22 to expand. In some embodiments, this method and pattern can be used to relieve pressure within pericardium 22, thereby treating conditions such as HFpEF. The shape of openings 28 can be anything that allows pericardium 22 to expand, e.g., ovals, circles, squares, rectangles, slits and the like. Any suitable quantity of openings 28 can be created. Openings 28 can be located in pericardium 22 anywhere on heart 20 as desired (including posterior regions not shown).

An additional method for partial removal of pericardium 22 can be performed as follows. The pericardial space can be entered by a catheter device, and two small hooks, clamps, or other retention devices (e.g., an Amplatzer-like device) can be installed to the pericardium. A cut to the pericardium can be made, and the catheter device can be positioned between the two small retention devices that were installed in the pericardium. Then the pericardium can be rolled up in a lateral direction by rotary action of the catheter device to create a bundle of pericardium—until a phrenic nerve is reached. The rolling can be stopped as soon as phrenic nerve stimulation is observed. Next, an outer sheath that acts as a cutting tool is placed around the bundle of pericardium. The cutting of the pericardium bundle will remove the pericardium portion and release the catheter device simultaneously.

In some cases, a clamp device can be used to help hold a portion of a pericardium in a region near an entry site. For example, a clamping device configured to be similar to an Amplatzer with larger patches in place of discs can be used to clamp at least a portion of a pericardium. In some cases, the two large patches can be connected between the center of the patches and/or along an outer perimeter of the patches. Once a clamp device is deployed, a user can tug on the clamp device to gain a secure hold on the pericardium and then insert an overtube that can be configured to cut the pericardium. In some cases, a clamp device can be used to enter the pericardium, and then poke back out of the pericardium. In some cases, two different clamp devices can be used at two different sites.

In some cases, a spreader device can be used to help increase a gap within the pericardial space. In some cases, a spreader device can include a number (e.g., 2, 3, 4, 5, 6, or more) expandable petals or blades. Once the spreader device enters the pericardial space with the petals or blades folded along a central axis of the device and positioned in a desired location, a balloon can be inflated such that petals or blades spread apart creating a gap within the pericardial space. In some cases, the balloon can be deflated such that the petals or blades fold along a central axis. In this case, the spreader device can be advanced to another position, and the balloon inflated again, thereby creating additional gaps or openings within the pericardial space. In some cases, one or more petals or blades can included a cutting component or electrodes that can be used to cut tissue as desired.

An additional method for partial removal of pericardium 22 can be performed as follows. The pericardial space can be entered by a catheter device, and two small hooks, clamps, or other retention devices (e.g., an Amplatzer-like device) can be installed to the pericardium. A cut to the pericardium can be made, and the catheter device can be positioned between the two small retention devices that were installed in the pericardium. Then the pericardium can be rolled up in a lateral direction by rotary action of the catheter device to create a bundle of pericardium—until a phrenic nerve is reached. The rolling can be stopped as soon as phrenic nerve stimulation is observed. Next, an outer sheath that acts as a cutting tool is placed around the bundle of pericardium. The cutting of the pericardium bundle will remove the pericardium portion and release the catheter device simultaneously.

Figure 22:
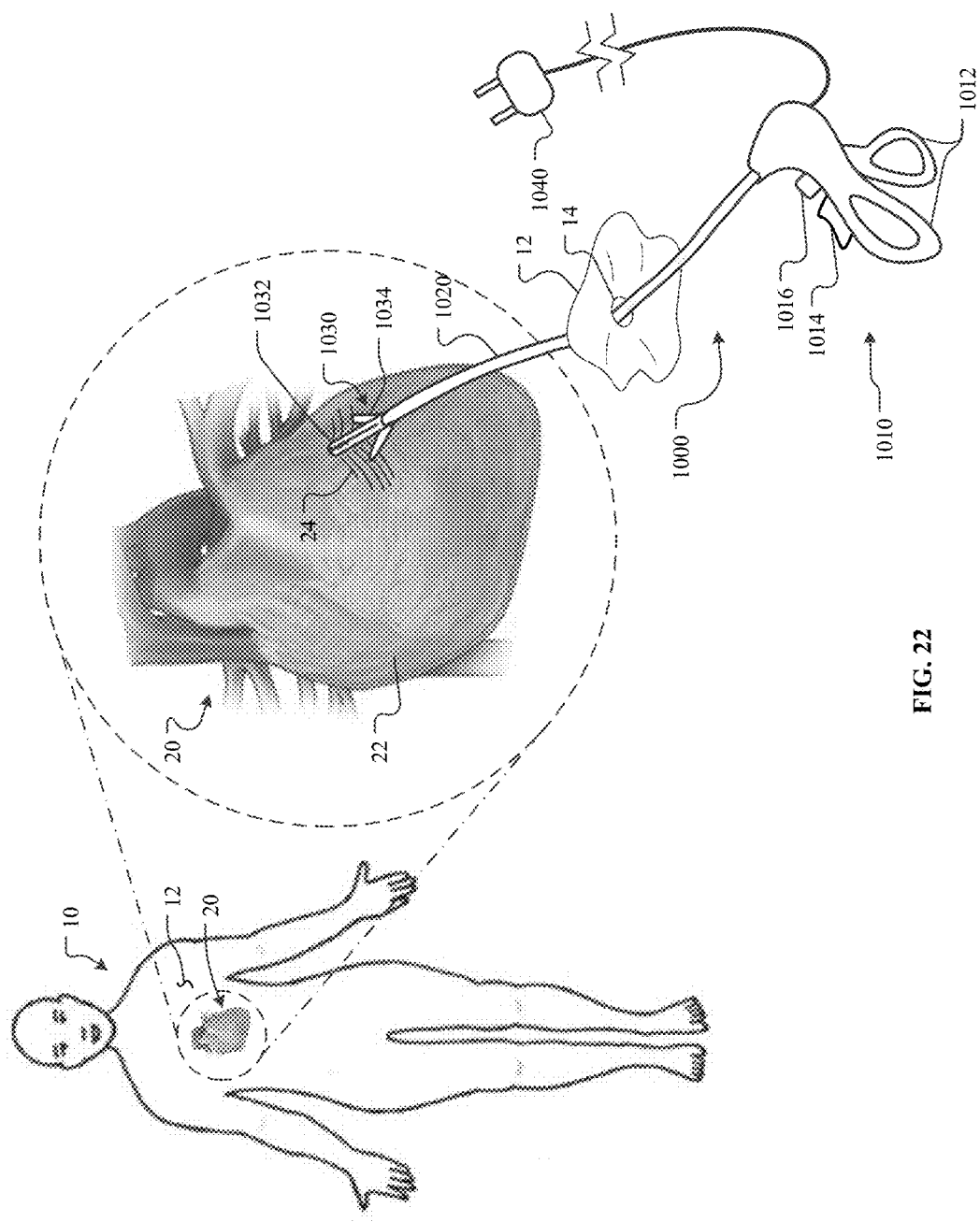
FIG. 22 is a schematic diagram of patient undergoing a pericardectomy using an exemplary catheter-based pericardectomy device system in accordance with some embodiments provided herein.

With reference to FIG. 22, a human patient 10 is depicted as undergoing a pericardectomy procedure using an example pericardectomy device 1000. Patient 10 has a skin surface 12, and a heart 20 that is encompassed by a pericardium 22.

Example pericardectomy device 1000 is a catheter-based device configured for percutaneous functionality. That is, pericardectomy device 1000 is insertable through a skin penetration point 14, such as an incision. In some cases, a trocar device is employed in skin penetration point 14. In some cases, a delivery sheath or endoscope is installed in patient 10 to direct the placement of the pericardectomy device 1000.

While pericardectomy device 1000 is depicted as a single catheter, in some embodiments two or more catheter-based devices are used to perform the pericardectomy procedures provided herein. In some cases, multiple skin penetration points may be employed. Still further, in some embodiments, an open-chest procedure, or a thoracoscopy procedure can be used to perform the pericardectomy procedures provided herein.

Example pericardectomy device 1000 includes an actuator 1010, a flexible catheter 1020, and an operative distal end 1030. In this example, operative end 1030 includes a grasping device 1032 and a cutting device 1034. Example pericardectomy device 1000 also includes a bipolar connection 1040 for energizing operative end 1030.

Some embodiments of the pericardial modification methods provided herein include provisions to avoid or minimize dissection or damage to particular structures such as the phrenic nerves or blood vessels. To facilitate avoidance of damage to structures such as the phrenic nerves, some embodiments of operative end 1030 include a device such as an electrode (not shown) that can be used to identify the location of the phrenic nerves. Phrenic nerves control the motor impulses to muscles of the diaphragm. When the electrode is in the proximity of the phrenic nerves, electrical pulses generated from the electrode will stimulate movement of the diaphragm that can be visualized by clinicians. Hence, when electrical pulses delivered by an electrode result in no movement of the diaphragm, it can be determined that the phrenic nerves are not in the immediate vicinity of operative end 1030. In such cases, grasping and cutting of the pericardium by operative end 1030 can be performed in the immediate vicinity with a low likelihood of incurring damage to the phrenic nerves.

In some cases, to identify and/or avoid damage to the vessels, an algorithm for vessel identification and turning off energy delivery can be used. In some cases, sensors such as Doppler probes or impedance measurements from electrograms can be used. For example, impedance from myocardium and pericardium can stay stable through the cardiac cycle for the most part, but a characteristic phasic variation can occur in any hollow viscus or as a result of change with contact or pressure or internal diameter. This can occur in arteries and can be used identify quickly where arteries are when a device provided herein is placed into position.

In some embodiments, squeezing the two handles 1012 together can close the grasping device 1032 to secure a portion of the pericardium 22. In some embodiments, grasping device 1032 is a forceps, and the jaws of the forceps can be closed by squeezing handles 1012 together. In some embodiments, grasping device 1032 can perform both grasping and cutting operations. For example, grasping device 1032 can be configured to grasp pericardium 22 using an initial amount of clamping force, and by applying a greater amount of force the jaws of grasping device 1032 can cut through pericardium 22.

In some embodiments, grasping device 1032 is a suction member that can retract pericardium 22. The suction force can be applied to pericardium 22 in a controllable fashion using actuator 1010. In some embodiments, other suitable types of grasping devices 1032, including cryogenic devices, are included with pericardectomy device 1000.

In some embodiments, grasping device 1032 is an electrocautery device. In such embodiments, a single grasping device 1032 can grasp, sever, and cauterize pericardium 22. Bipolar connection 1040 can be connected to an energy source, such as a RF cautery system power supply. The electrocautery operation can be initiated by a clinician operator using actuator 1010, such as by pushing a button 1016.

In some embodiments, some or all of catheter 1020 is steerable. For example, in some embodiments operative end 1030 is steerable using actuator 1010. In some such embodiments, grasping device 1032 can be canted away from heart 20 to create a pericardium tent 24. That is, after grasping device 1032 has secured a portion of pericardium 22, the clinician operator of pericardectomy device 1000 can steer operative end 1030 to pull pericardium 22 away from heart 20 to create a tent-like portion of pericardium 24.

In some embodiments, a balloon device (not shown) can be used to create pericardium tent 24. For example, an un-inflated balloon can be positioned in the pericardial space. Then the balloon can be inflated to create pericardium tent 24. In some embodiments, the inflation of the balloon can be used to expand or tear a hole or incision that was made in the pericardium.

In some embodiments, one side of the balloon device can include one or more RF electrodes. The side of the balloon with the one or more RF electrodes can be positioned abutting the underside of pericardium 22. The RF electrodes can be activated to damage parietal pericardium. Alternately, the orientation of the balloon can be reversed and the RF electrodes can perform ablation of the epicardial pericardium.

Pericardium tent 24 facilitates the isolation of a portion of pericardium 22 so that the cutting of pericardium 22 can occur with less risk of damaging other tissues. In some embodiments, a stabilizing device (not shown) can also be used to reduce movement of pericardium 22 in preparation for cutting.

Cutting device 1034 can be located at a position at operative end 1030 to cooperate with grasping device 1032. For example, in some embodiments, cutting device 1034 is locatable between the jaws of grasping device 1032. In some embodiments, cutting device 1034 is locatable adjacent to grasping device 1032. In this manner, cutting device 1034 can be in position to cut pericardium tent 24 created by grasping device 1032. In some embodiment, cutting device 1034 is locatable and maneuverable independent of grasping device 1032.

Cutting device 1034 can be actuated by a clinician operator using actuator 1010. For example, in some embodiments pulling a trigger 1014 can operate cutting device 1034. In some embodiments after cutting, the exposed edges of pericardium 22 can be cauterized using pericardectomy device 1000.

A variety of types of cutting devices 1034 can be used. In some embodiments, cutting device 1034 is a scissors tool. In some embodiments, cutting device 1034 is a scalpel blade. In some embodiments, the tip(s) of cutting device 1034 have sharp points. In some embodiments, the tip(s) of cutting device 1034 have blunt points. In some embodiments, cutting device 1034 is a snare or lasso that can be positionally maneuvered axially and radially on catheter 1020. The snare can be used to capture and cinch portions of pericardium tent 24, and then cut it. In some embodiments, the snare can also cauterize pericardium 22. In some embodiments, other suitable types of cutting devices are used on pericardectomy device 1000.

In some embodiments, the pericardial sac 22 is initially punctured by a device (e.g., grasping device 1032 or cutting device 1034), then the cutting is performed from within the pericardial space, and in a direction generally outward and away from heart tissue.

In some embodiments of pericardectomy device 1000, two opposing catheters are used. One catheter can have its tip positioned in the pericardial space to create pericardium tent 24. A second catheter can be located external to the pericardial space and can perform grasping/cutting operations on pericardium tent 24. In some embodiments, the opposing catheters are magnetically coupled to each other to coordinate their relative positions in an advantageous manner. In some embodiments, the opposing catheters are mechanically coupled together, or in other suitable manners, to coordinate their relative positions.

After a single cut or multiple cuts to pericardium 22 have been made, pericardectomy device 1000 can be repositioned to another area of pericardium 22 as desired. The actions can be repeated to cut (or tear, puncture, dissect, etc.) another portion of pericardium 22. By repeating the actions described herein, pericardium 22 can be removed to the extent desired—which may be a full or partial removal of pericardium 22.

Figure 23:
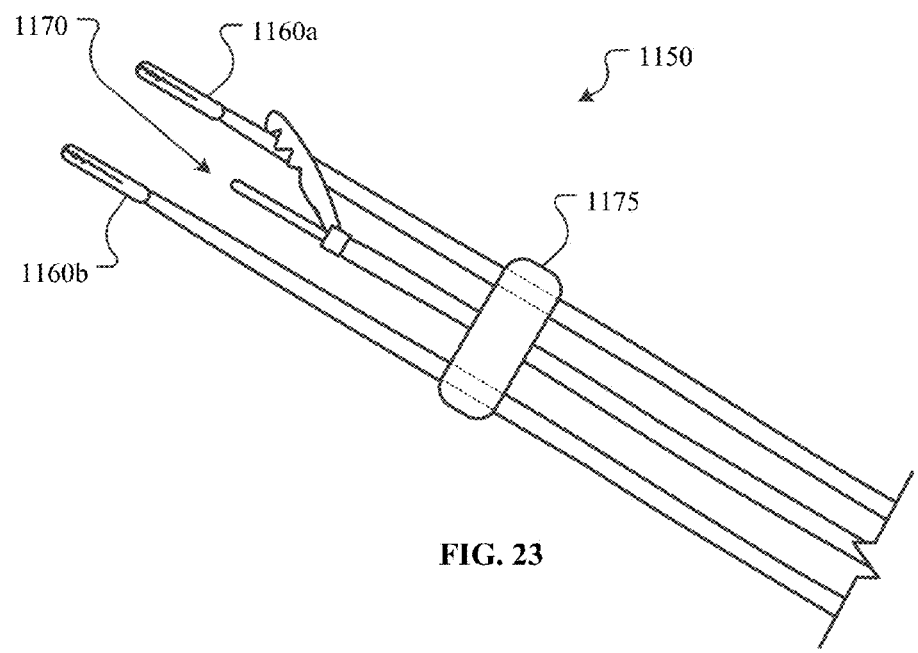
FIGS. 23 and 24 are schematic illustrations of another exemplary pericardectomy device system in accordance with some embodiments provided herein.
Figure 24:
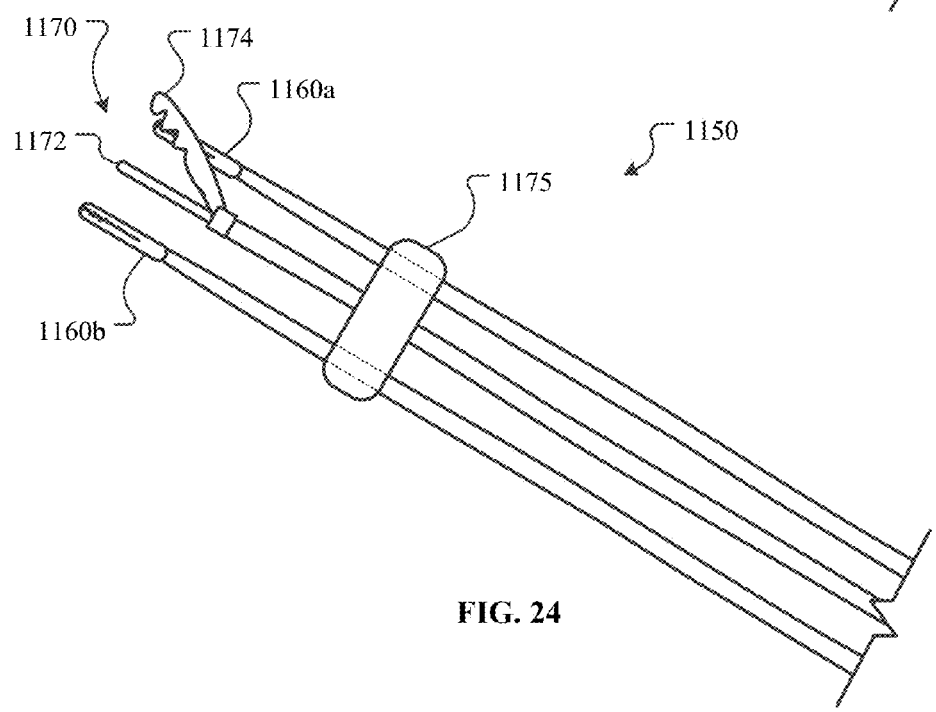

With reference to FIGS. 23 and 24, another example pericardectomy device 1150 is provided. Pericardectomy device 1150 includes two graspers 1160a and 1160b that flank the position of a central electrocautery tissue cutter 1170. In some embodiments, the orientation of graspers 1160a-b to cutter 1170 can be controlled by a coupler 1175, or in some embodiments by an over-tube device. In some embodiments, coupler 1175 is fixedly coupled to cutter 1170 and slidably coupled to graspers 1160a-b. In some embodiments, an endoscope and light source are included with pericardectomy device 1150. In some embodiments, central electrocautery tissue cutter 1170 is also used as a probe that is used to stimulate the phrenic nerve so as to detect and map the location of the phrenic nerves.

In some embodiments, pericardectomy device 1150 can include one or more electrodes that can be used to trace electrical potentials on tissues such as the pericardial tissue. In some implementations, such tracing of electrical potentials can be useful for navigation of pericardectomy device 1150 within the patient.

In some embodiments, graspers 1160a-b are over-the-wire grasping tools. In other words, graspers 1160a-b can be installed over a guidewire device. In some embodiments, graspers 1160a-b are configured for a monorail-type guidewire system. In some embodiments, graspers 1160a-b are configured for a central wire advancement guidewire system. That is, graspers 1160a-b can include a longitudinal lumen that can slidably receive a guidewire, or graspers 1160a-b can include a collar that can slidably receive a guidewire. In some embodiments, only one jaw of graspers 1160a-b is pivotable, while the other jaw is fixed. In some embodiments, both jaws of graspers 1160a-b are pivotable.

In some embodiments, suction devices can be used instead of or in addition to graspers 1160a-b having jaws.

In some embodiments, the longitudinal lumen of graspers 1160a-b that are so equipped can be used to convey a contrast media for fluoroscopy. In some such embodiments, the lumen can be confluent with the jaws of graspers 1160a-b. When pericardectomy device 1150 is in use, the contrast media can be used to visualize that one jaw of graspers 1160a-b is above the pericardium and the other jaw is below the pericardium as desired. That is, the jaw beneath the pericardium can be visualized by the contrast media being contained within the pericardial space, and the jaw above the pericardium can be visualized by the contrast media being dispersed outside of the pericardial space. In some embodiments, contract media can be delivered through one or both graspers 1160a-b while graspers 1160a-b are engaged with pericardial tissue. This delivery of contrast media can stain the pericardial tissue to enhance the radiographical visualization thereof.

To maneuver pericardectomy device 1150 into position near the outer surface of the patient's pericardium, first the guidewire can be percutaneously installed. After installing the guidewire to the pericardial space, a first grasper 1160a can be advanced over the guidewire, and the grasper 1160a can be clamped onto a portion of pericardium. Then grasper 1160a can be detached from the guidewire (assuming a monorail-type guidewire system). The second grasper 1160b can then be advanced over the same guidewire, and clamped onto a portion of pericardium adjacent to the other grasper 1160a. Then a single overtube device or coupler 1175 can be installed onto the shafts of graspers 1160a-b. Coupler 1175 can include a central cutting tool such as electrocautery tissue cutter 1170. Electrocautery tissue cutter 1170 can be advanced to the area of graspers 1160a-b. Alternatively, in some implementations two or more guidewires can be utilized. In some such implementations, graspers 1160a-b and tissue cutter 1170 can thereby be advanced over guidewires that are distinct from each other.

The general operation of pericardectomy device 1150 can be as follows (this description assumes that pericardectomy device 1150 is already within a patient and near the outer surface of the patient's pericardium). A clinician can manipulate graspers 1160a-b to advance them beyond cutter 1170 as shown in the configuration of FIG. 23. Graspers 1160a-b can slide in relation to coupler 1175 (or an overtube device) to thereby advance beyond cutter 1170. Graspers 1160a-b can be used to grasp or pinch a portion of the pericardium. With portions of pericardial tissue contained within the jaws of graspers 1160a-b, a pericardial tent is formed between graspers 1160a-b.

Next, cutter 1170 can be advanced by the clinician to a location generally adjacent to graspers 1160a-b as shown in FIG. 24. A probe 1172 of cutter 1170 can puncture the pericardial tent. Then a jaw 1174 of cutter 1170 can be pivoted by the clinician to come into contact with the pericardial tent. Energy for bi-polar electrocauterization can be delivered to cutter 1170 to sever and cauterized the pericardial tissue contained between probe 1172 and jaw 1174. After the cutting, the clinician can open the jaws of graspers 1160a-b, and then advance graspers 1160a-b to the next desired location to be cut. The configuration of pericardectomy device 1150 can then once again resemble FIG. 23. The process steps above can be repeated until the pericardial cutting is completed to the extent desired.

After completion of the cutting process, or at one or more times during the cutting process, portions of pericardial tissue can be severed and removed from the patient. This severing and removal of the pericardial tissue can be performed using various techniques. In one example, a bipolar snare tool (not shown, but similar to those devices used for removing polyps) can be advanced over graspers 1160a-b while graspers 1160a-b are holding pericardial tissue. The bipolar snare tool can be advanced beyond the distal end of graspers 1160a-b and into contact with the pericardial tissue. The bipolar snare tool can be activated while the graspers 1160a-b continue to hold the pericardial tissue. After the energy from bipolar snare tool has severed a portion of the pericardial tissue, graspers 1160a-b can be withdrawn from the patient while the portion of the pericardial tissue is in the jaws of graspers 1160a-b.

Figure 25:
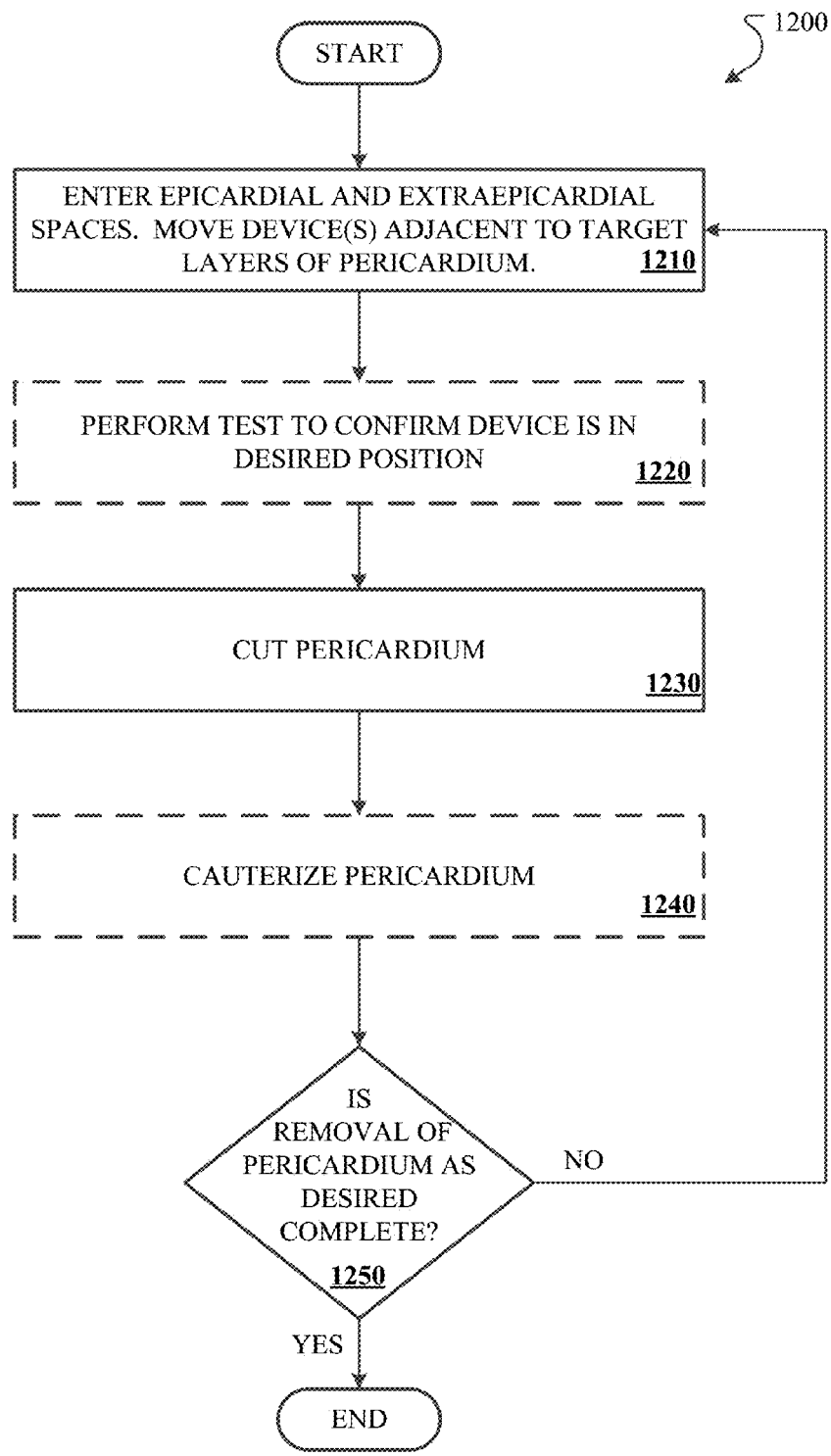
FIG. 25 is flowchart of a pericardectomy method in accordance with some embodiments provided herein.

FIG. 25 is a flowchart of an example embodiment of a method 1200 for performing a pericardial modification using the devices provided herein. In general, method 1200 can be performed percutaneously or by an open-chest procedure. Method 1200 can be used to remove all or a partial portion of one or both pericardial layers. Method 1200 can be used to remove pericardium that is diseased, and/or pericardium that is healthy.

At operation 1210, a device enters the epicardial and/or extraepicardial spaces and is moved into position adjacent to the pericardium. In some embodiments, a catheter-based device is used. In some embodiments, other types of surgical devices can be used. In some embodiments, a combination of catheter-based devices and other surgical devices can be used. In some embodiments, the device includes grasping and cutting functionality. In some embodiments, a balloon device is included on the device. In some embodiments, sensory functionalities are included on the device, such as Doppler, impedance, and pacing probes to provide a few examples. In some embodiments, a camera device is included on the device. In some embodiments, the device includes electrocautery or cryogenic capabilities. The device may include any combination and subcombination of such functional features, as well as other features that are advantageous for performing pericardectomy procedures.

At operation 1220, a test is optionally performed to confirm that the device is in a desired location for cutting the pericardium. For instance, phrenic nerves generally located on the sides of the heart can be advantageously avoided using tests to confirm their location. For example, in some embodiments the device can include a pacing probe to stimulate the area of the tip of the device. If the tip of the device is in the proximity of a phrenic nerve, a movement of the diaphragm may be observed in response to electrical stimulation from the pacing probe. In other cases, other devices such as a Doppler or impedance probe and the like may be optionally used to confirm the device is in a desired location for cutting the pericardium.

In some cases, a device provided herein can be positioned such that the distal end portion is laying adjacent to the targeted layers of the pericardium to be modified to help avoid injuring parts of anatomy other than the pericardium. For example, the distal end portion of a cutting device can be positioned to avoid cutting a phrenic nerve, a coronary vessel, or another sensitive structure. For example, in some cases cardiac rhythms can be monitored to determine whether the position of a pacing probe indicates that myocardium is being energized by the pacing signals. In this manner, steps can be taken to avoid damaging myocardium. In another example, in some cases pacing can be used to determine the position of, and to avoid damage to, a vagus nerve. For example, physiological parameters such as, but not limited to, heart rate, blood pressure, and/or EKG patterns (e.g., P-R intervals) can be monitored. Changes to such parameters can be indicative of proximity to a vagus nerve, and steps can be taken to avoid damaging the vagus nerve.

At operation 1230, the pericardium is cut, torn, punctured, burned, or otherwise locally destructed to create an opening in the pericardium. In some cases, a cutting device is used to sever the pericardium. In some cases, an electrocautery device can be used to burn an opening in the pericardium. In some cases, other devices including lasers, cryogenic devices, and other cutting tools can be used to create openings in the pericardium.

At operation 1240, the edges of pericardium can be optionally cauterized. In some cases, cauterization may beneficially inhibit the reformation of pericardial tissue across the openings created in the pericardium.

At operation 1250, the clinician can determine whether the pericardium has been modified as desired, or whether further treatment is desired. For example, in some cases such a determination can be made at least in part based on one or more intraoperative tests that can be performed to assess the effect(s) of the pericardial modifications made during the performance of method 1200. Such intraoperative tests are described elsewhere herein. When further treatment is desired, for example to make additional cuts in the pericardium to facilitate removal of pericardium, the clinician can generally repeat method 1200 until the pericardectomy procedure is complete.

It is usually very fibrous near the sub-xiphoid space. In some cases, the methods provided herein can include entering into the pericardium near the sub-xiphoid access point and then exiting once the device progresses past the fibrous area. For example, a device provided herein can include a small hypotube that has a hollow needle within it. A wire can be positioned within the hollow needle. A distal end region of the wire can include an electrode with RF to help pierce through the tissue.

In some cases, a method provided herein can be performed in a manner that reduces bleeding and/or pain during and/or after the procedure. For example, a pericardial sheath can be used that is coated with an agent that acts as a sponge (e.g., a chemical sponge) to soak up blood and/or prevent bleeding. In some cases, the agent can be a thrombostatic agent. Examples of coating agents include, without limitation, gelfoam (purified porcine skin gelatin), human thrombin, and bovine thrombin. In some cases, an RF catheter of a device provided herein can be configured to elute a steroid, depo-medrone, ionized lidocaine, lidocaine, and/or bupivacaine, as well as any liquid combination comprised of the former. Removing the pericardium itself can help reduce post-procedural pain because the pain fibers are being removed along with it. In some cases, removal of the pericardium can become adjunct to other procedures (e.g., left atrial appendage closure or intractable angina treatment) to reduce pain. If some of the pericardium is left behind, however, (for example, areas near the phrenic nerve), low DC energy can be delivered to reduce and/or destroy pain fibers. Such energy can be delivered as described herein. In some embodiments, the pericardial modification devices and methods provided herein involve modification of the pericardium rather than pericardectomy. Such modification techniques can have value in actually keeping the pericardial space and structures intact but greatly minimizing pericardial restraint. One example pericardial modification procedure can be performed as follows.

First, a balloon device can be positioned in the pericardial space. The balloon device can include electrodes on at least one of the balloon's surfaces. Some electrodes can be orientated so they are pointed toward the pericardial space. Then, those electrode are stimulated for the purposes of mapping the course of the phrenic nerve. Those electrodes are then taken away from the energy delivering circuit with a switching system.

Other electrodes on the balloon are then used to deliver energy to the parietal pericardium. The energy could be radiofrequency ("RF"), ultrasound, or DC current at either electroporative or ablation dose levels. In some embodiments, the balloon itself can be differentially expandable. That is, the balloon can expand so as to exert substantial pressure against the parietal pericardial surface, but only minimal pressure towards the surface of the heart, to avoid coronary compression. This pericardial modification method can provide a combination of parietal pericardium dilation, breaking of the fibrous pericardium, and DC/RF softening of the pericardium (which in turn allows more dilation).

In some cases, the methods and devices provided herein can be used to access the pericardium using a mediastinal approach, a pericardial window, and/or an open pericardial access approach, for example, when some other surgery is being performed or contemplated. In some cases, the methods and devices provided herein can be used to access the pericardium from the heart itself. For example, the methods and devices provided herein can be used to exit the heart, suction in or grasp at least a portion of the pericardium, and remove it via an endocardial approach. In such cases, a closure device can be positioned in the exit site of the heart once the procedure is completed.

In some cases, the methods and devices provided herein can be used to cut or modify the pericardium without extracting the pericardium. For example, once cut or modified, the pericardium can be left in the space in a manner where it can no longer impede myocardial relaxation.

In some cases, a stimulation device can be used to control the phrenic nerve. For example, a sub-threshold stimulation device can be used to improve diaphragmatic function in patients with diaphragmatic problems. Stimulating the phrenic nerve in a synchronous manner with the cardiac cycle can be performed. For example, a wire placed on both phrenic nerves for cross-shunting purposes can be used to treat unilateral phrenic palsy. In some cases, electrodes can be placed on the phrenic nerve on both sides, and a central wire can be used as a shunt between the two of them. In these cases, if one phrenic nerve is paretic, then the impulse from the other phrenic nerve can be shunted down towards the diaphragm. This wire can include an electrically active element to provide for passage of current from one stimulated nerve to the contralateral side. This can be at any level, including more distal to the damage section to provide ability for nerve functional recovery.

Figure 26:
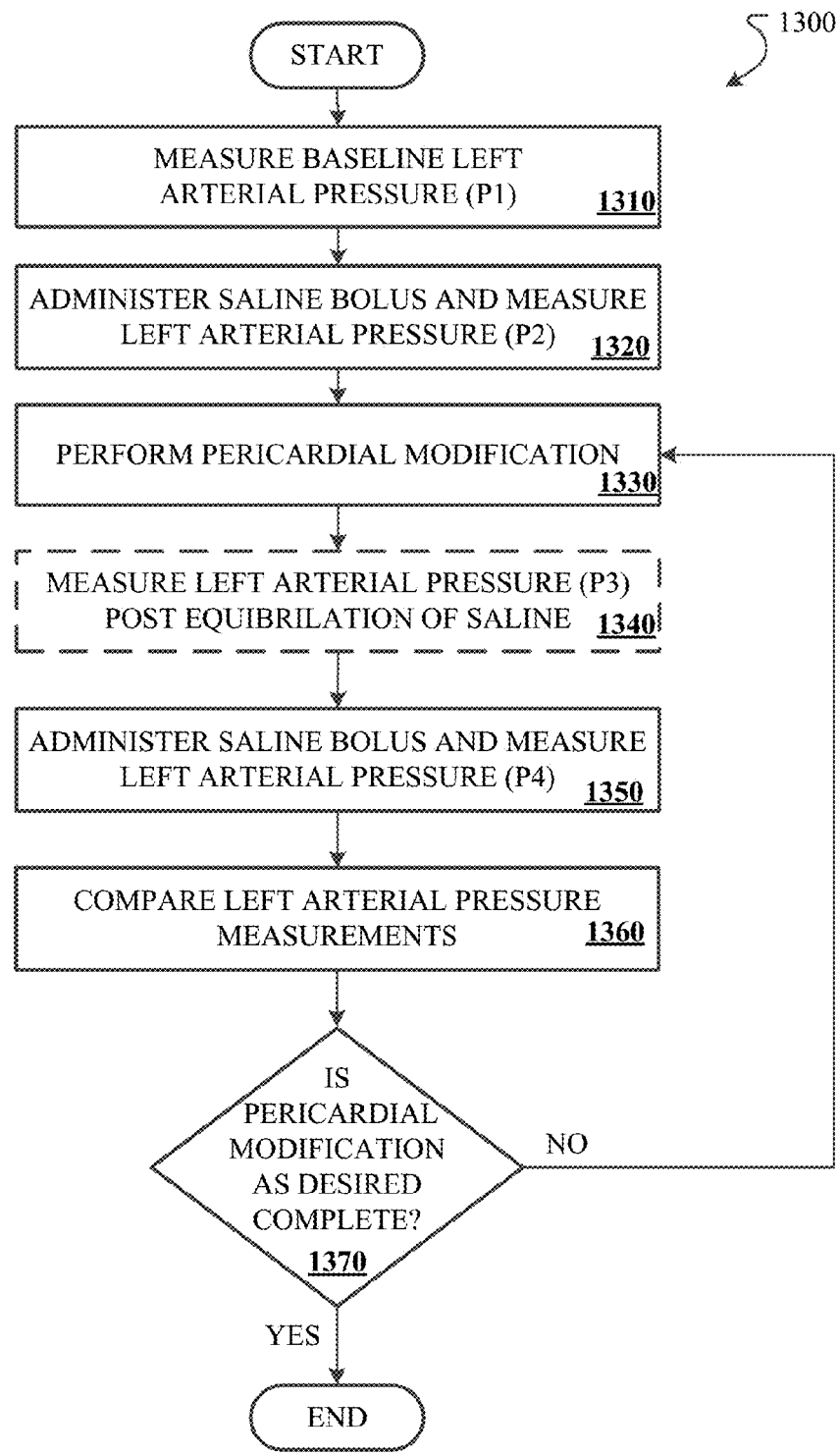
FIG. 26 is flowchart of another pericardectomy method in accordance with some embodiments provided herein.

FIG. 26 is a flowchart of an example embodiment of a method 1300 for performing a pericardial modification using the devices provided herein. In general, method 1300 can be performed percutaneously or by an open-chest procedure. Method 1300 can be used to remove all or a partial portion of one or both pericardial layers. Method 1300 can be used to remove pericardium that is diseased, and/or pericardium that is healthy. Method 1300 includes steps for assessing the efficacy of the pericardial modification.

At operation 1310, the left arterial pressure (hereinafter "P1") is measured. This measurement is used as a baseline for comparison(s) later on in method 1300. In some embodiments, one or more other parameters in addition to, or in the alternative to, the left arterial pressure are measured (with analogous objectives). For example, in some embodiments parameters such as, but not limited to, pulmonary wedge pressure, left ventricle volume, left ventricular contractility, intra-pericardial pressure, ventricular septum geometry, ventricular free wall geometry, size of particular portions of the heart, excursions of particular portions of the heart, other hemodynamic measurements, and the like, and combinations thereof are measured at operation 1310.

At operation 1320, a bolus of saline is administered and the measurement performed at operation 1310 is repeated while the saline effects are occurring. In some cases, the saline can be infused relatively rapidly. For example, in some cases an IV bolus of about 500 ml can be infused in about 10-20 minutes. While the effects of the saline bolus are occurring, the measurement performed at operation 1310 is repeated. For example, in some cases the left arterial pressure (hereinafter "P2") is measured while the effects of the saline bolus are occurring. In some cases, when P2 is greater than P1, HFpEF is indicated.

At operation 1330, pericardial modification is performed. The pericardial modification can be performed using any of the devices and systems described herein (and analogs), and can be performed in accordance with any of the techniques described herein (and analogs). For example, in some cases the pericardial modification can be performed in accordance with method 1200 described above. The pericardial modification can be a single cut, multiple cuts, removal of one or more portions of pericardium, removal of the entire pericardium, and variations on any type and/or combination of such types of pericardial modification.

At optional step 1340, the left arterial pressure (hereinafter "P3"), and/or other type of measurement(s), can be measured after the effects of the saline bolus have substantially subsided. In some cases, measures to accelerate the subsidence of the saline bolus can be implemented. For example, in some cases substances can be administered. Such substances can include, but are not limited to, diuretics, nitroglycerine, nitropeptides, opioids, and the like. Moreover, other measures to accelerate the subsidence of the saline bolus can include, but are not limited to, adjusting patient ventilation to increase peek-end-expiratory-pressure (PEEP) or to decrease inspiratory/expiratory time ratio. In some cases, a single lung can be ventilated to accelerate the subsidence of the saline bolus.

At operation 1350, a second bolus of saline is administered (as in operation 1320) and the measurement performed at operation 1310 is repeated while the saline effects are occurring. For example, in some cases the left arterial pressure (hereinafter "P4") is measured while the effects of the second saline bolus are occurring.

At operations 1360 and 1370, the aforementioned measurements that were obtained at operations 1310, 1320, 1340 (optionally), and 1350 are compared, and a determination is made regarding whether the pericardial modification has yielded a desired effect. By comparing such measurements (e.g., P1, P2, P3, and P4), the efficacy of the pericardial modification performed at operation 1330 can be assessed. For example, without limitation, when P4 is substantially similar to P1, then the pericardial modification may be determined to be satisfactorily completed. In contrast, if P4 is substantially greater than P1, then additional pericardial modification may be desirable (by returning to operation 1330 as shown). Further, if P4 is less than P2 to a desired extend, then the pericardial modification may be determined to be satisfactorily completed. It should be understood that such comparisons are merely provided for illustrative purposes, and that other measurements and measurement criteria can be additionally or alternatively used to determine whether the pericardial modification has been satisfactorily completed.

In another example, a technique for determining whether the pericardial modification has been satisfactorily completed can include (but need not be limited to) recording and comparing the electrical activity of the phrenic nerve before and after pericardial modification. That is, pre and post pericardial modification electroneurograms of the phrenic nerve can be captured using, in some cases, the pericardial modification devices provided herein (e.g., as described above in reference to pericardium slitter device 500 et al.). First (prior to pericardial modification), a baseline electroneurogram of the phrenic nerve can be recorded. Then the pericardial modification can be performed. Thereafter, a second electroneurogram of the phrenic nerve can be recorded. In some cases, if the electrical activity of the second electroneurogram is sufficiently lessened in comparison to the electrical activity of the baseline electroneurogram, then the pericardial modification may be determined to be satisfactorily completed. In contrast, if the electrical activity of the second electroneurogram is substantially the same as the electrical activity of the baseline electroneurogram, then the pericardial modification may be determined to be unsatisfactorily completed (and further pericardial modification may be performed).

In another example, a technique for determining whether the pericardial modification has been satisfactorily completed can include (but need not be limited to) visualizing the shape of the ventricular septum pre and post pericardial modification. Such visualization can be performed via sonographic imaging, for example. In some such cases, without limitation, an echocardiogram is performed to visualize the shape of the ventricular septum. In some cases, the echocardiogram can be performed using a suitably equipped pericardial modification device as described herein. That is, in some embodiments, one or more ultrasonic transducers can be included on the pericardial modification devices described herein. Alternatively, or additionally, in some cases a device separate from a pericardial modification device is used for visualizing the shape of the ventricular septum. In a typical, healthy heart, the ventricular septum is convex from the perspective of the right ventricle. In contrast, the ventricular septum of a heart with greater than normal pericardial constraint may appear more flat. Hence, while prior to a pericardial modification the ventricular septum may appear more flat than normal, after the pericardial modification the ventricular septum may become more convex-shaped from the perspective of the right ventricle. In some cases, the shape of the ventricular septum can be quantified. In any event, in some cases, by comparing the pre and post pericardial modification shape of the ventricular septum, a determination of whether the pericardial modification has been satisfactorily completed can be made or assisted.

Additional Features for Inclusion in Some Device and/or Method Embodiments

In some cases, the performance of the devices and systems provided herein can be enhanced by installing a tenting balloon member (not shown) within the pericardial space. When such a tenting balloon member is inflated, it creates a pericardial tissue tent. The resulting tent can draw the pericardium 22 towards the tenting balloon member such that the pericardium 22 is tighter in the region of the pericardium cutting devices provided herein. In some cases, the increased tautness of the pericardium 22 can enhance the performance of the cutting devices. In some cases, a second balloon can be introduced within the pericardial space. This can be done on the same surface/side as the active cutting device to provide stability/fulcrum on the epicardial surface and to force the cutting device towards the pericardial sac. In some cases, there can be two balloons in combination on the same side or different sides at varying distances (possibly even on a sliding rail) so as to provide stability for cutting and enhanced safety.

In some cases, a flat disc-like balloon member (not shown) can be used at the pericardial opening 23 to enlarge the opening to pericardium 22. For example, the flat disc-like balloon member can be positioned at pericardial opening 23 and then the flat disc-like balloon member can be inflated. In doing so, pericardium 22 will be torn as the flat disc-like balloon member enlarges. In some embodiments, the flat disc-like balloon member is asymmetrical (e.g., essentially triangular).

In some cases in accordance with the devices, systems and methods provided herein, electrodes on balloons and other devices are used for ablation or electroporation to modify the pericardium. In result, the parietal and/or visceral pericardium loses some elasticity.

In some cases, a hemi-spherical balloon with electrodes on the spherical surface can be used within the pericardial space. For example, prior to full inflation of the balloon, the electrodes can be oriented to face the visceral pericardium to apply ablation or electroporation to the visceral pericardium (to modify the visceral pericardium as described above). Thereafter, the hemi-spherical balloon can be oriented and inflated such that the spherical surface faces and stretches the parietal pericardium. Once it reaches its limit for stretching, then the electrodes can be energized to ablate or electroporate the parietal pericardium. After that, the hemi-spherical balloon can be further inflated to stretch the parietal pericardium even more. This technique modifies the parietal pericardium without cutting it (instead, the elastic force of the parietal pericardium is removed).

In some cases, magnetic portions, coatings, or films can be used on the devices provided herein (e.g., catheters, shafts, etc.). The magnetic areas can be advantageously used to make two or more devices attracted to each other, or to make two or more devices repel each other. The magnetism can provide the option of two accesses to the pericardial space while magnetically interlocking devices installed in the two access points. This can prevent the two devices from rolling over on each other.

In some cases, distal ends or mid-ends of the sheaths can have interlocking segments that can engage inside the pericardium to allow for restriction of the proximal portions of the sheaths, while allowing "Y" shaped (e.g., about 30-120 degree) angulation of the distal ends of the sheaths to form diversion of the ends of the sheaths and space for cutting, accessing, and resection.

In some cases, the devices and methods provided herein include placement of a wedge-like device that be pressed against the apex of the heart and/or free floating in the pericardial space after looping through the transverse sinus for stability. The wedge-like device provides a fulcrum with two lumens/ports through which any of the dissection tools themselves or sheaths could fit and be used to aid in steerability/guidance. The ports/holes can have varying inflow and outflow openings to allow for direct insertion of the cutting tools and exit at angles to create more widespread dissection/grabbing/resection around the heart to occur.

In some cases, a transient pericardial dilatation test can be used as an acute trial option for patients or screening for effectiveness of this approach. Alternatively, this can be a serial process occurring over multiple visits as a temporary therapy. The goal of the transient pericardial dilatation test is to use our access sheath to instill fluid in an inflatable balloons to cause stretching and widening of the pericardial sac. This would also provide the additive function of keeping the pericardium intact prior to a full procedure or during the trial phase of the therapy. In addition to balloon inflation, this approach can include injecting a non-irritating fluid to the pericardial sac, as well as a draining/suctioning of the fluid to remove once the procedure is finished. The fluid can vary in temperature, composition. This could include but not be limited to cooled saline, a combination of lidocaine/saline, as well as anti-inflammatory or steroid injection to provide numbing as well as reduce inflammation/inflammatory response from the procedure. This approach can also be used prior to full resection if there is already pericardial restraint/thickening as a means to provide additional room in the pericardial sac to facilitate full resection.

The real-time efficacy/completeness of the procedure can be accessed. This would involve the use of an instillation into the pericardial sac of a small amount of microbubbles, microspheres, agitated saline, and/or contrast dye via lumens of the devices provided herein. At the end of resection, or when resection is thought to be completed, visibility of these structures (which can be activated with ultrasound at varying mechanical index to provide real-time imaging of injection into the prior pericardial space and out into the mediastinum) indicates full resection. If there is continued containment of these microbubbles (or contrast dye), this would indicate that additional resection needs to be performed.

Some embodiments of the pericardial modification methods provided herein include provisions to avoid or minimize dissection or damage to particular structures such as the phrenic nerves or blood vessels. To facilitate avoidance of damage to structures such as the phrenic nerves, some embodiments include a device such as an electrode (not shown) that can be used to identify the location of the phrenic nerves. Phrenic nerves control the motor impulses to muscles of the diaphragm. When the electrode is in the proximity of the phrenic nerves, electrical pulses generated from the electrode will stimulate movement of the diaphragm that can be visualized by clinicians. Hence, when electrical pulses delivered by an electrode result in no movement of the diaphragm, it can be determined that the phrenic nerves are not in the immediate vicinity. In such cases, grasping and cutting of the pericardium can be performed in the immediate vicinity with a low likelihood of incurring damage to the phrenic nerves.

In some cases, to identify and/or avoid damage to the vessels, an algorithm for vessel identification and turning off energy delivery can be used. In some cases, sensors such as Doppler probes or impedance measurements from electrograms can be used. For example, impedance from myocardium and pericardium can stay stable through the cardiac cycle for the most part, but a characteristic phasic variation can occur in any hollow viscus or as a result of change with contact or pressure or internal diameter. This can occur in arteries and can be used identify quickly where arteries are when a device provided herein is placed into position.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A method of treating a patient with heart failure with preserved ejection fraction, the patient having a chest, a heart and a pericardium, the method comprising:
   advancing a pericardial modification device into the patient's chest to the pericardium, wherein the pericardial modification device comprises:
   a control handle;
   a shaft extending from the control handle and having a distal end; and
   a distal end effector attached to the distal end of the shaft, the distal end effector including an upper jaw and a lower jaw that are controllably pivotable in relation to each other between: (i) a closed configuration in which respective cutting edges of the upper and lower jaws are essentially approximated with each other and (ii) an open configuration in which the respective cutting edges are spaced apart from each other, wherein relative pivoting motions between the upper and lower jaws are actuatable at the control handle, and wherein the distal end effector also includes a lower jaw extension that is distally extendable and retractable from the lower jaw;
   identifying a path on the pericardium that is free of tissue other than the pericardium;
   positioning the lower jaw under the pericardium and the upper jaw over the pericardium, wherein the positioning is performed while the lower jaw extension is distally extended;
   indirectly visualizing the upper and lower jaws to confirm their respective positions on opposing sides of the pericardium;

modifying the pericardium along the path to reduce pericardial restraint on the heart by actuating the control handle to pivot the upper and lower jaws relative to each other such that the respective cutting edges shear the pericardium to form one or more elongate slits in the pericardium;

measuring a hemodynamic effect of the modifying; and determining, based on the hemodynamic effect of the modifying, whether additional pericardial modification is needed to further reduce pericardial restraint on the heart.

2. The method of claim 1, wherein the pericardial modification device is advanced into the patient's chest percutaneously.

3. The method of claim 2, wherein the pericardial modification device is advanced into the patient's chest through a sub-xiphoidal incision.

4. The method of claim 1, further comprising indirectly visualizing the pericardial modification device during the advancing and during the modifying.

5. The method of claim 1, wherein the modifying is a first modifying, and wherein the method further comprises performing a second modifying of the pericardium in response to the determining that additional pericardial modification is needed to further reduce pericardial restraint on the heart.

6. The method of claim 1, wherein the measuring the hemodynamic effect of the modifying comprises measuring a left ventricular pressure prior to and after infusing a bolus of saline into the patient.

7. The method of claim 1, wherein said identifying a path on the pericardium that is free of tissue other than the pericardium comprises identifying a location of and avoiding one or more of a phrenic nerve, a coronary artery, a vagus nerve, and lung tissue.

8. The method of claim 1, wherein the lower jaw extension remains under an un-slit portion of the pericardium after individual ones of the one or more slits are formed.

9. The method of claim 1, wherein the respective positions of the upper and lower jaws are ascertained by observing tactile resistance to pushing the distal end effector while applying counter traction to the pericardium.

10. The method of claim 1, wherein said indirectly visualizing the respective positions of the upper and lower jaws comprises injecting contrast media on either side of the pericardium under fluoroscopy.

11. The method of claim 10, wherein the contrast media is injected under the pericardium via a lumen in the lower jaw of the distal end effector.

12. The method of claim 10, wherein contrast media is injected over the pericardium via a lumen in the upper jaw of the distal end effector.

13. The method of claim 1, wherein the lower jaw extension is retracted while at least one of the one or more elongate slits is formed.

14. The method of claim 1, wherein the lower jaw of the distal end effector is advanced over a guide wire disposed under the pericardium such that the lower jaw remains under the pericardium after the elongate one or more slits are formed.

15. The method of claim 1, wherein the one or more elongate slits are formed in the pericardium from an inferior point to one or more superior points, and wherein the inferior point is adjacent a xiphoid between lungs and the one or more superior points are adjacent a pericardial reflection.

16. The method of claim 1, wherein said identifying a path on the pericardium that is free of tissue other than the pericardium comprises:
delivering electrical stimulation to tissue; and
observing for a response resulting from said delivering electrical stimulation to tissue.

17. The method of claim 16, wherein said observing for a response comprises observing for a change in respiration indicative of phrenic nerve stimulation.

18. The method of claim 16, wherein said observing for a response comprises observing for a change in cardiac rhythm indicative of myocardium stimulation.

19. The method of claim 16, wherein said observing for a response comprises observing for a change in at least one of heart rate, blood pressure and EKG P-R interval indicative of vagus nerve stimulation.

20. The method of claim 1, wherein said identifying a path on the pericardium that is free of tissue other than the pericardium comprises using Doppler imaging.

21. The method of claim 20, wherein the Doppler imaging is provided via an ultrasound transducer disposed on the pericardial modification device.

22. The method of claim 20, wherein the Doppler imaging detects coronary vasculature.

23. The method of claim 1, wherein said identifying a path on the pericardium that is free of tissue other than the pericardium comprises performance of impedance mapping.

24. The method of claim 1, wherein the lower jaw extension is distally extendable and retractable from the lower jaw by actuating the control handle.

* * * * *